(12) United States Patent
Sauvé et al.

(10) Patent No.: US 7,022,680 B2
(45) Date of Patent: Apr. 4, 2006

(54) INHIBITORS OF ADP-RIBOSYL TRANSFERASES, CYCLASES, AND HYDROLASES

(75) Inventors: Anthony A. Sauvé, Bronx, NY (US); Vern L. Schramm, New Rochelle, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 10/158,636

(22) Filed: May 30, 2002

(65) Prior Publication Data

US 2003/0229033 A1    Dec. 11, 2003

(51) Int. Cl.
   A01N 43/04   (2006.01)
   A61K 31/70   (2006.01)
   C07H 19/00   (2006.01)
   C07H 21/00   (2006.01)

(52) U.S. Cl. .......................... 514/42; 514/43; 514/45; 514/46; 514/47; 514/48; 514/49; 514/50; 514/51; 514/52; 536/22.1; 536/26.1; 536/26.2; 536/26.21; 536/26.24; 536/27.1; 536/28.1

(58) Field of Classification Search .................. 514/42, 514/43, 45, 46, 47, 48, 49, 50, 51, 52; 536/22.1, 536/26.1, 26.2, 26.24
See application file for complete search history.

(56) References Cited

U.S. PATENT DOCUMENTS

| 5,569,650 | A | | 10/1996 | Watanabe et al. |
| 5,679,394 | A | | 10/1997 | Long, Jr. et al. |
| 6,103,701 | A | * | 8/2000 | von Borstel et al. .......... 514/46 |
| 2002/0132783 | A1 | | 9/2002 | Sauve et al. |

OTHER PUBLICATIONS

Sauve et al., "A Covalent Intermediate in CD38 is Responsible for ADP-Ribosylation and Cyclization Reactions", J. of the American Chemical Society, vol. 122, No. 33, Aug. 23, 2000.*
Sauve et al., J. Am. Chem. Soc., Vol. 122, pp. 7855-7859, 2000.*
Ashamu et al., Roles for adenosine ribose hydroxyl groups in cyclic adenosine 5'-diphosphate ribose-mediated Ca2+ release. Biochemistry, 36:9509-9517, 1997.
Bailey et al., Cyclic aristeromycin diphosphate ribose: a potent and poorly hydrolysable Ca2+-mobilising mimic of cyclic adenosine diphoshate ribose. FEBS Lett., 379:227-230, 1996.
Berthelier et al., Human CD38 is an authentic NAD(P)+ glycohydrolase. Biochem J., 330:1383-1390, 1998.
Clapper et al., Pyridine nucleotide metabolities stimulate calcium release from sea urchin egg microsomes desensitized to inositol trisphosphate. J. Biol. Chem., 262: 9561-9568, 1987.

Cockayne et al. Mice deficient for the ecto-nicotinamide adenine dinucleotide glycohydrolase CD38 exhibit altered humoral immune responses. Blood, 92:1324-1333, 1998.
Fernandez et al., Analysis of the distribution of human CD38 and of its ligand CD31 in normal tissues. J. Biol. Regul. Homeostatic Agents, 12:81-91, 1998.
Fox et al., Nucleosides. XII. Direct synthesis of 2'-deoxycytidine and its alpha-anomer. J. Am. Chem. Soc., 83:4066-4070, 1961.
Galione et al., Ca2+-induced Ca2+ release in sea urchin egg homogenates: modulation by cyclic ADP-ribose. Science, 253:1143-1146, 1991.
Handlon, and Oppenheimer, Substituent effects on the pH-independent hydrolysis of 2'-substituted nicotinamide arabinosides. J. Org. Chem., 56:5009-5010, 1991.

(Continued)

*Primary Examiner*—James O. Wilson
*Assistant Examiner*—Traviss C. McIntosh, III
(74) *Attorney, Agent, or Firm*—Amster, Rothstein & Ebenstein LLP

(57) ABSTRACT

The present invention provides compounds having the formula:

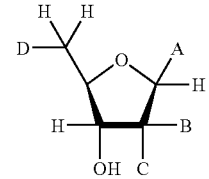

wherein A is a nitrogen-, oxygen-, or sulfur-linked aryl, alkyl, cyclic, or heterocyclic group, the group being further substituted with an electron contributing moiety; B is hydrogen, or a halogen, amino, or thiol group; C is hydrogen, or a halogen, amino, or thiol group; and D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge.

The present invention also provides pharmaceutical compositions containing the above compounds, methods of using the above compounds as pharmaceuticals, and processes for preparing the above compounds.

Also provided are methods for inhibiting an ADP-ribosyl transferase, ADP-ribosyl cyclase, ADP-ribosyl hydrolase, or NAD-dependent deacetylase enzyme, and methods for treating a disease or condition associated with an ADP-ribosyl transferase, ADP-ribosyl cyclase, ADP-ribosyl hydrolase, or NAD-dependent deacetylase enzyme in a subject in need of treatment thereof.

29 Claims, 8 Drawing Sheets

OTHER PUBLICATIONS

Hara-Yokoyama et al., Complex gangliosides as cell surface inhibitors for the Ecto-NAD+ glycohydrolase of CD38. Biochemistry, 40:888-895, 2001.

Howard et al., Formation and hydrolysis of cyclic ADP-ribose catalyzed by lymphocyte antigen CD38. Science, 262:1056-1059, 1993.

Itoh et al., Molecular cloning of murine BST-1 having homology with CD38 and Aplysia ADP-ribosyl cyclase. Biochem. Biophys. Res. Commun., 203:1309-1317, 1994.

Jackson and Bell, Isolation of a cDNA encoding the human CD38 (T10) molecule, a cell surface glycoprotein with an unusual discontinuous pattern of expression during lymphocyte differentiation. J. Immunol., 144:2811-2815, 1990.

Jiang et al., Membrane-permeant esters of phosphatidylinositol 3,4,5-trisphosphate. J. Biol. Chem., 273:11017-11024, 1998.

Kaisho et al., BST-1, a surface molecule of bone marrow stromal cell lines that facilitates pre-B-cell growth. Proc. Natl. Acad. Sci. USA, 91:5325-5329, 1994.

Kang et al., Synthesis and biological activity of bis (pivaloyloxymethyl) ester of 2'-azido-2'-deoxyuridine 5'-monophosphate. Nucleosides & Nucleotides, 17:1089-1098, 1998.

Kato et al., Regulatory role of CD38 (ADP-ribosyl cyclase/cyclic ADP-ribose hydrolase) in insulin secretion by glucose in pancreatic beta-cells. J. Biol. Chem., 270:30045-30050, 1995.

Khoo and Chang, Localization of plasma membrane CD38 is domain specific in rat hepatocyte. Arch. Biochem. Biophys., 373:35-43, 2000.

Kruppa et al., Bioactivatable derivatives of 8-substituted cAMP-analogues. Bioorg. Med. Chem. Lett., 7:945-948, 1997.

Lee, Modulator and messenger functions of cyclic ADP-ribose in calcium signaling. Recent Prog. Horm. Res., 51: 355-388, 1996.

Lee, Physiological functions of cyclic ADP-ribose and NAAADP as calcium messengers. Annu. Rev. Pharmacol. Toxicol., 41:317-345, 2001.

Lee and Aarhus, ADP-ribosyl cyclase: an enzyme that cyclizes NAD+ into a calcium-mobilizing metabolite. Cell Regul., 2:203-209, 1991.

Lee and Aarhus, Fluorescent analogs of NAADP with calcium mobilizing activity. Biochim. Biophys. Acta., 1425: 263-271, 1998.

Lee and Levitt, The crystal structure of cyclic ADP-ribose. Nature Struct. Biol., 1:143-144, 1994.

Li et al., Membrane-permeant esters of inositol polyphosphates, chemical syntheses and biological applications. Tetrahedron, 53:12017-12040, 1997.

Mehta et al., Human CD38, a cell-surface protein with multiple functions. FASEB J., 10:1408-1417, 1996.

Merkler et al., The rate constant describing slow-onset inhibition of yeast AMP deaminase by coformycin analogues is independent on inhibitor structure. Biochemistry, 29:8358-8364, 1990.

Mizuguchi et al., Neuronal localization of CD38 antigen in the human brain. Brain Res., 697:235-240, 1995.

Muller-Steffner et al., Slow-binding inhibition of NAD+ glycohydrolase by arabino analogues of beta-NAD. J. Biol. Chem., 267:9606-9611, 1992.

Munshi et al., Characterization of the active site of ADP-ribosyl cyclase. J. Biol. Chem., 274:30770-30777, 1999.

Normark et al., How neutrophils recognize bacteria and move toward infection. Nat. Med., 7:1182-1184, 2001.

Okamoto, The CD38-cyclic ADP-ribose signaling system in insulin secretion. Mol. Cell. Biochem., 193:115-118, 1999.

Oppenhemer and Handlon, Mechanism of NAD-dependent enzymes. In The Enzymes, Sigman, D.L. Ed., Academic Press Inc: San Diego CA, Chapter 10, vol. 20, pp 453-505, 1992.

Partida-Sanchez et al., Cyclic ADP-ribose production by CD38 regulates intracellular calcium release, extracellular calcium influx and chemotaxis in neutrophils and is required for bacterial clearance in vivo. Nat. Med., 7:1209-1216, 2001.

Porter et al., Identification of the active site nucleophile in nucleoside 2-deoxyribosyltransferase as glutamic acid 98. J. Biol. Chem., 270:15551-15556, 1995.

Reyes-Harde et al. Evidence of a role for cyclic ADP-ribose in long-term synaptic depression in hippocampus. Proc. Natl. Acad. Sci. USA, 96:4061-4066, 1999.

Rusinko and Lee, Widespread occurrence in animal tissues of an enzyme catalyzing the conversion of NAD+ into a cyclic metabolite with intracellular Ca2+-mobilizing activity. J. Biol. Chem., 264:11725-11731, 1989.

Sato et al., Inhibitor peptide SNP-1 binds to a soluble form of BST-1/CD157 at a 2:2 stoichiometry. Eur J Biochem, 264:439-445, 1999.

Sato et al., Novel peptide inhibitor of ecto-ADP-ribosyl cyclase of bone marrow stromal cell antigen-1 (BST-1/CD157). Biochem. J., 337:491-496, 1999.

Sauve et al., The reaction mechanism for CD38. A single intermediate is responsible for cyclization, hydrolysis, and base-exchange chemistries. Biochemistry, 37:13239-13249, 1998.

Sauve et al., A covalent intermediate in CD38 is responsible for ADP-ribosylation and cyclization reactions. J. Am. Chem. Soc., 122:7855-7859, 2000.

Sethi et al., 7-Deaza-8-bromo-cyclic ADP-ribose, the first membrane-permeant, hydrolysis-resistant cyclic ADP-ribose antagonist. J. Biol. Chem., 272:16358-16363, 1997.

Sleath et al., Pyridine coenzyme analogues. 3. Synthesis of three NAD+ analogues containing a 2'-deoxy-2'-substituted nicotinamide arabinofuranosyl moiety. J. Org. Chem., 56: 3608-3613, 1991.

States et al., Similarities in amino acid sequences of Aplysia ADP-ribosyl cyclase and human lymphocyte antigen CD38. Trends Biochem. Sci., 17:495-497, 1992.

Sun et al., CD38/ADP-ribosyl cyclase: a new role in the regulation of osteoclastic bone resorption. Cell. Biol., 146: 1161-1171, 1999.

Wall et al., Inhibition of the intrinsic NAD+ glycohydrolase activity of CD38 by carbocyclic NAD analogues. Biochem. J., 335:631-636, 1998.

Walseth and Lee, Synthesis and characterization of antagonists of cyclic-ADP-ribose-induced Ca2+ release. Biochim. Biophys. Acta., 1178:235-242, 1993.

Walseth et al., Identification of Cyclic ADP-ribose-binding proteins by photoaffinity labeling. J. Biol. Chem., 268: 26686-26691, 1993.

Wong et al., Cyclic 3-deaza-adenosine diphosphoribose: a potent and stable analog of cyclic ADP-ribose. Biochim. Biophys. Acta, 1472:555-564, 1999.

Wu et al., Abscisic acid signaling through cyclic ADP-ribose in plants. Science, 278:2126-2130, 1997.

Yamamoto-Katayama et al., Crystallographic studies on human BST-1/CD157 with ADP-ribosyl cyclase and NAD glycohydrolase activities. J. Mol. Biol., 316:711-723, 2002.

Zechel and Withers, Glycosidase mechanisms: anatomy of a finely tuned catalyst. Acc. Chem. Res., 33:11-18, 2000.

Lee et al., "Structural Determination of a Cyclic Metabolite of NAD+ with Intracelluler Ca2+-mobilizing Activity." Journal of Biological Chemistry 264, 3:1608-1615 (1989).

Prasad et al., "Crystal Structure of Aplysia ADP Ribosyl Cyclase, a Homologue of the Bifunctional Ectozyme CD38." Nature Structural Biology 3, 11: 957-964 (1996).

Muller-Steffner et al., "Mechanism of Cyclization of Pyridine Nucleotides by Bovine Spleen NAD+ Glycohydrolase." Journal of Biological Chemistry 271, 39: 23967-23972 (1996).

Kim et al., "Synthesis and Degradation of Cyclic ADP-Ribose by NAD Glycohydrolases." Science 261:1330-1333 (1993).

Niedballa et al., "A General Synthesis of N-Glycosides.I.1 Synthesis of Pyrimidine Nucleosides." J. Org. Chem. 39, 25:3654-3660 (1974).

Morrison et al., "The Behavior and Significance of Slow-Binding Enzyme Inhibitors." An Interscience Publication, 61:201-300 (1998).

Wong et al., "Identification of Glu-540 as the Catalytic Nucleophile of Human β-Glucuronidase Using Electrospray Mass Spectrometry." Journal of Biological Chemistry 273, 51:34057-34062 (1998).

Withers et al., "Identification of a Covalent -D-Glucopyranosyl Enzyme Intermediate Formed on a -Glucosidase." J. Am. Chem. 110:8551-8553 (1988).

Berthelier et al., "Probing Ligand-Induced Conformational Changes of Human CD38." Eur. J. Biochem. 267:3056-3064 (2000).

Lund et al., "CD38: A New Paradigm in Lymphocyte Activation and Signal Transduction." Immunological Reviews, 161:79-93 (1988).

Lee et al., "Structures and Activities of Cyclic ADP-Ribose, NAADP and Their Metabolic Enzymes." Mol. Cell. Biochem, 193:89-98 (1999).

Togo et al., "A Facile Preparative Method of C-Nucleosides." Chemistry Letters, 1673-1676 (1992).

* cited by examiner

1: X= H, Y = CONH$_2$
2: X = Me, Y = CONH$_2$
3: X = H, Y = H

INHIBITORS OF ADP-RIBOSYL TRANSFERASES, CYCLASES, AND HYDROLASES

STATEMENT OF GOVERNMENT INTEREST

This invention was made with government support under NIH Grant Nos. GM19335 and AI34342. As such, the United States government has certain rights in this invention.

BACKGROUND (1) Field of the Invention

The present invention generally relates to inhibitors of ADP-ribosyl transferases, cyclases and hydrolases, and NAD-dependent deacetylases, including CD38. More specifically, the invention relates to improved inhibitors of those enzymes, where the inhibitors are designed according to the mechanism of the enzymes' action.

(2) Description of the Related Art

References Cited

Ashamu, G. A., Sethi, J. K., Galione, A., and Potter, B. V. L. (1997) *Biochemistry*, 36, 9509–9517.

Bailey, V. C., Fortt, S. M., Summerhill, R. J., Galione, A., and Potter, B. V .L. (1996) *FEBS Lett.* 379, 227–228.

Bethelier, V., Tixier, J. M., Muller-Steffner, H., Schuber, F., and Deterre, P. (1998) *Biochem J.* 330, 1383–1390.

Clapper, D. L., Walseth, T. F., Dargie, P. J., and Lee, H. C. (1987) *J. Biol. Chem.* 262, 9561–9568.

Cockayne et al. (1998) *Blood* 92, 1324–1333.

Fernandez, J. E., Deaglio, S., Donati, D., Saoboda Beusan, I., and Corno, F. (1998) *J. Biol. Regul. Homeostatic Agents* 12, 81–91.

Fox, J. J., Yung, N. C., Wempen, I., and Hoffer, M. (1961) *J. Am. Chem. Soc* 83, 4066–4072.

Galione, A., Lee, H. C., and Busa, W. B. (1997) *Science* 253, 1143–1146.

Handlon, A. L., Oppenheimer, N. J. (1991) *J. Org. Chem.* 56, 5009–5010.

Hara-Yokoyama, M., Nagatsuka, Y., Katsumata, O. Irie, F., Kontani, K., Hoshino, S., Katada, T., Ono, Y., Fujita-Yoshhigaki, J., Sugiya, H., Furuyama, S., and Hirabayashi, Y.(2001) *Biochemistry* 40, 888–95.

Howard, M., Grimaldi, J. C., Bazan, J. F., Lund, F. E., and Santos-Argumedo, L. (1993) *Science* 262, 1056–1059.

Itoh, M., Ishihara, K., Tomzawa, H., Tanaka, H., Kobune, Y., and Ishikawa, J. (1994) *Biochem. Biophys. Res. Commun.* 203, 1309–1317.

Jackson, D. G., and Bell, J. I. (1990) *J. Immunol.* 144, 2811–2815.

Jiang et al. (1998) *J. Biol. Chem.* 273, 11017.

Kaisho, T., Ishikawa, J., Oritani, K., Inazawa, J., Tomizawa, H., and Muroaka, O. (1994) *Proc. Natl. Acad. Sci. USA* 91, 5325–5329.

Kang et al. (1998) *Nucleosides Nucleotides* 17, 1089.

Kato, I., Takasawa, S., Akabane, A., Tanaka, O., and Abe, H. (1995) *J. Biol. Chem.* 270, 30045–30050.

Khoo, K. M., and Chang, C. F. (2000) *Arch. Biochem. Biophys.* 373, 35–43.

Kruppa et al. (1997) *Bioorg. Med. Chem. Lett.* 7, 945.

Lee, H. C. (1996) *Recent Prog. Horm. Res.* 51, 355–388.

Lee, H. C. (2001) *Annu. Rev. Pharmacol. Toxicol.* 41, 317–345.

Lee, H. C., and Aarhus, R.(1991) *Cell Regul.* 2, 203–209.

Lee, H. C., and Aarhus, R.(1998) *Biochim. Biophys. Acta* 1425, 263–271.

Lee, H. C., Aarhus, R., and Levitt, D. (1994) *Nature Struct. Biol.* 1, 143–144.

Lee et al. (1997) *Tetrahedron* 53, 12017.

Mehta et al. (1996) *FASEB J.* 10, 1408–1417.

Merkler et al. (1990) *Biochemistry* 29, 8358–8364.

Mizuguchi, M., Otsuka, N., Sato, M., Ishii, Y., and Kon, S. (1995) *Brain Res.* 697, 235–240.

Muller-Steffner, H. M., Malver, O., Hosie, L., Oppenheimer, N. J. and Schuber. F. (1992) *J. Biol. Chem.* 267, 9606–9611.

Munshi, C., Theil, D., Mathews, I. J., Aarhus, R., Walseth, T. F, and Lee, H. C. (1999) *J. Biol. Chem.* 274, 30770–30777.

Normark, S., Normark, B. H., and Hornet, M. (2001) *Nat. Med.* 11, 1182–1184.

Okamoto, H. (1999) *Mol. Cell. Biochem.* 193, 115–118.

Oppenhemer, N. J., Handlon, A. L. In *The Enzymes*, Sigman, D. L. Ed., Academic Press Inc: San Diego Calif., 1992, Chapter 10, vol 20, pp 453–505.

Partida-Sanchez, S., Cockayne, D. A., Monard, S., Jacobson, E. L., Oppenheimer, N., Garvy, B., Kusserm K., Goodrich, S., Howard, M., Harmsen, A., Randall, T. D., and Lund, F. E. (2001) *Nat. Med.* 11, 1209–1216.

Porter, D. J., Merrill, B. M., and Short, S. A. (1995) *J. Biol. Chem.* 270, 15551–15556.

Reyes-Harde et al. (1999) *Proc. Natl. Acad. Sci. USA* 96, 4061–4066.

Rusinko, N., and Lee, H. C. (1989) *J. Biol. Chem.* 264, 11725–11731.

Sato, A., Yamamoto, S., Kajimura, N., Oda, M., Usukura, J., and Jingami, H. (1999a) *Eur J Biochem* 264, 439–45.

Sato, A., Yamamoto, S., Ishihara, K., Hirano, T., J., and Jingami, H. (1999b) *Biochem. J.* 337, 491–6.

Sauve, A. A., Munshi, C., Lee, H. C., and Schramm, V. L. (1998) *Biochemistry* 37, 13239–13249.

Sauve, A. A. Deng, H. T., Angeletti, R. H., and Schramm, V. L. (2000) *J. Am. Chem. Soc.* 122, 7855–7859.

Sethi, J. K., Empson, R. M., Bailey, V. C., Potter, B. V. L., and Galione, A. (1997) *J. Biol. Chem.* 272, 16358–16363.

Sleath, P. R., Handlon, A. L., and Oppenheimer, N. J. (1991) *J. Org. Chem.* 56, 3608–3613.

States, D. J., Walseth, T. F., and Lee, H. C. (1992) *Trends Biochem. Sci.* 17, 495.

Sun et al. (1999) *Cell. Biol.* 146, 1161–1171.

Wall, K. A., Klis, M., Kornet, J., Coyle, D., Ame, J. C., Jacobson, M. K., and Slama, J. T. (1998) *Biochem. J.* 335, 631–636.

Walseth, T. F., and Lee, H. C. (1993) *Biochim. Biophys. Acta* 1178, 235–242.

Walseth, T. F., Aarhus, R., Kerr, J. A., and Lee, H. C. (1993) *J. Biol. Chem.* 268, 26686–26691.

Withers, S. G. (2000) *Acc. Chem. Res.* 33, 11–18.

Wong, L., Aarhus R., Lee H. C., and Walseth, T. F. (1999) *Biochim. Biophys. Acta* 1472, 555–64.

Wu, Y., Kuzma, J., Marechal, E., Graeff, R., and Lee, H. C. (1997) *Science* 278, 2126–2130.

Yamamoto-Katayama, S., Ariyoshi, M., Ishihara, K., Hirano, T., Jingami, H., and Morikawa, K. (2002) *J. Mol. Biol.* 316, 711–723.

CD38 is a membrane anchored homodimeric ectoenzyme common to a variety of immune cells (Jackson and Bell, 1990) and other tissues (Fernandez et al., 1998) including pancreas (Kato et al., 1995) kidney (Khoo and Chang, 2000) and brain (Mizuguchi et al., 1995). CD38 is homologous to BST-1 (Kaisho et al., 1994; Itoh et al., 1994), bone stromal cell antigen, and invertebrate ADP-ribosyl cyclases (Lee and Aarhus, 1991; States et al., 1992) and catalyzes the formation of cyclic-ADP-ribose (cADPR, Lee et al., 1994) from $NAD^+$ (Scheme 1, Rusinke and Lee, 1989). cADPR is a potent second messenger that directly activates $Ca^{+2}$ release inside of cells via an $IP_3$ independent mechanism (Lee, 2001; Lee, 1995; Clapper et al., 1987) thought to be mediated by ryanodine receptors (Lee, 2001). Recent evidence indicates that cADPR and CD38 plays a crucial role in the human immune response by activation of the cell-mediated neutrophil response to bacterial infection (Partida-Sanchez et al., 2001) and associated inflammatory physiology (Id.; Normark et al., 2001). ADP-ribosyl-cyclase and cADPR signaling has also been demonstrated in plants as mediator of the abscisic acid activated stress response (Wu et al., 1997).

dent deacetylases were found to have several advantages to the above nucleotide-based inhibitors (U.S. patent application Ser. No. 10/038,760, incorporated by reference in its entirety). Those inhibitors react rapidly to form a covalent intermediate that cannot cyclize and that are relatively stable to hydrolysis, thereby trapping the enzyme in a catalytically-inactive form. Further development of these mechanism-based inhibitors to provide highly stabile, potent inhibitors of ADP-ribosyl transferases, cyclases and hydrolases, and NAD-dependent deacetylases is desirable.

SUMMARY OF THE INVENTION

Accordingly, the inventors have discovered that providing an electron-contributing moiety to the leaving group of the mechanism-based inhibitors described in U.S. patent appli-

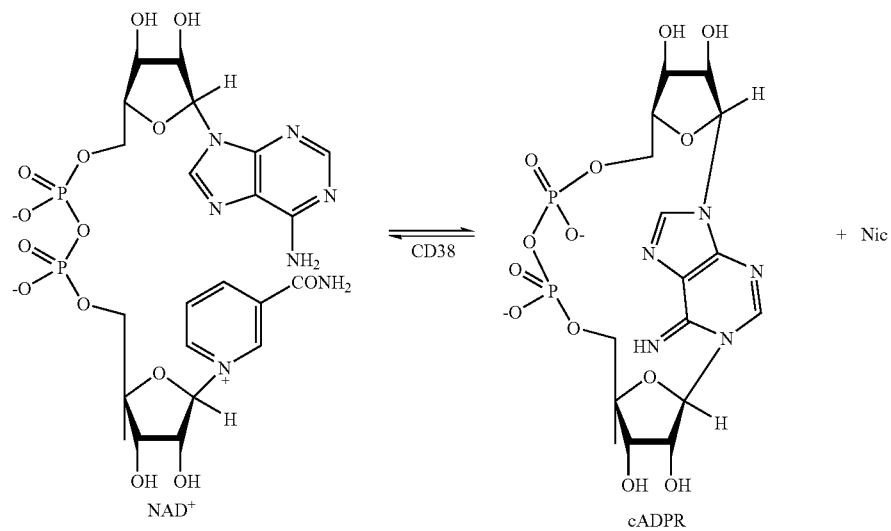

Scheme 1

Not surprisingly, the ADP-ribosyl cyclases have been targets for inhibitor design (Sleath et al., 1991; Muller-Steffner et al., 1992; Bethelier et al., 1998; Wall et al., 1998; Sauve et al., 2000). Also, analogs of cADPR with antagonistic (Sato et al., 1999a; Sato et al., 1999b; Hara-Yokoyama et al., 2001; Walseth and Lee, 1993), or agonistic (Sethi et al., 1997; Walseth et al., 1993; Ashamu et al., 1997; Galione et al., 1997; Wong et al., 1999; Lee and Aarhus, 1998; Baily et al., 1996) properties have been reported. Most of the inhibitors and cADPR analogs are phosphorylated compounds (Lee, 2001), and have practical limitations affecting their use in whole cell or whole tissue investigations, because of the difficulty of passing charges across cell membranes (Id.). Although altered inhibitor structure to nucleosides could potentially make compounds more cell permeant, no reports of nucleoside-based CD38 or ADP-ribosyl-cyclase inhibitors have appeared.

In prior work, the mononucleotide ara-F-NMN$^+$ was shown to be a potent inhibitor of CD38 with a $K_i$ value of 61 nM (Sauve et al., 2000). This $K_i$ is similar to the dinucleotide inhibitor ara-F-NAD$^+$ (Sleath et al., 1991), where a $K_i$ value of 169 nM was reported (Muller-Steffner et al., 1992).

In other work, mechanism-based inhibitors of ADP-ribosyl transferases, cyclases and hydrolases, and NAD-depencaton Ser. No. 10/038,760 (the '760 application) greatly stabilizes the compounds to hydrolysis. The resulting improved inhibitors provide greater potential for therapeutic benefits, and provides improved reagents for studying ADP-ribosyl transferases, cyclases and hydrolases, and NAD-dependent deacetylases, including CD38.

Thus, in some embodiments, the present invention is directed to compounds represented by the formula:

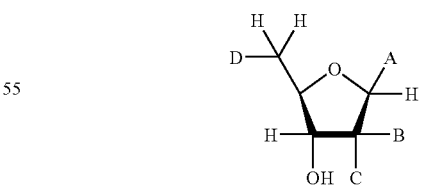

wherein A is a nitrogen-, oxygen-, or sulfur-linked aryl, alkyl, cyclic, or heterocyclic group. In these embodiments, the group A is further substituted with an electron contributing moiety. Additionally, B is hydrogen, or a halogen, amino, or thiol group; C is hydrogen, or a halogen, amino, or thiol group; and D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge. The compounds are preferably inhibitors of ADP-ribosyl transferase, ADP-ribosyl cyclase, ADP-ribosyl hydrolase, and/or NAD-dependent deacetylase enzymes. Pharmaceutical compositions comprising these compounds and a pharmaceutically acceptable carrier are also encompassed by the invention.

In other embodiments, the invention is directed to methods for inhibiting an ADP-ribosyl transferase, ADP-ribosyl cyclase, ADP-ribosyl hydrolase or an NAD-dependent deacetylase enzyme. The methods comprise contacting the enzyme with an amount of the above compound of claim 2 effective to inhibit the enzyme.

Additionally, the invention is directed to methods for treating a disease or condition associated with an ADP-ribosyl transferase, ADP-ribosyl cyclase, ADP-ribosyl hydrolase, or NAD-dependent deacetylase enzyme in a subject in need of treatment thereof. These methods comprise administering to the subject the above-described inhibitor compound in an amount effective to treat the disease or condition.

DETAILED DESCRIPTION OF THE INVENTION

Figure 1:
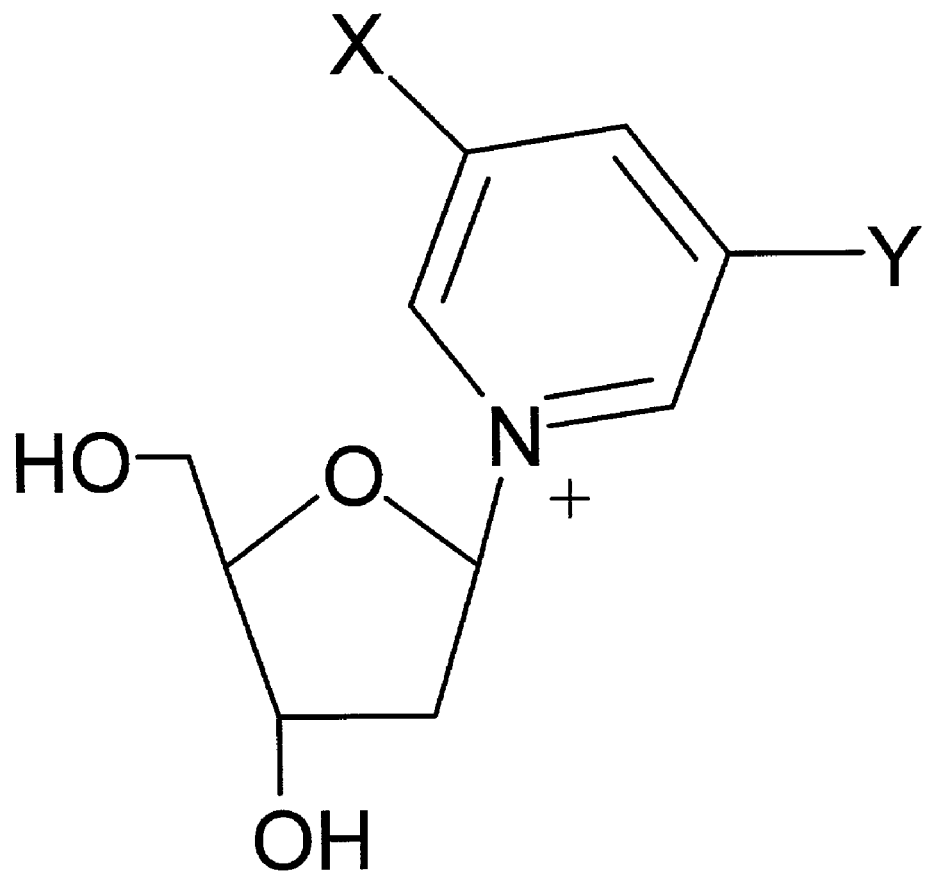
FIG. 1 provides the structure of inhibitors 1–3.

The present invention provides improvements to the mechanism-based inhibitors of ADP-ribosyl cyclases, ADP-ribosyl hydrolases, ADP-ribosyl transferases, and NAD-dependent deacetylases first disclosed in U.S. patent application Ser. No. 10/038,760 (the '760 application). The improvements are based on the discovery that the stability of the inhibitors can be improved by substituting the leaving group of the inhibitors with an electron-contributing moiety. Without being limited to any particular mechanism for the improved stability, it is believed that the electron-contributing moiety improves stability of the inhibitors by causing a decrease in the hydrolysis of the leaving group from the rest of the inhibitor.

Thus, in one aspect, the present invention provides compounds having the formula:

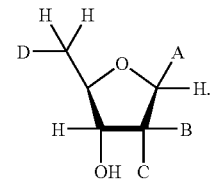

In these embodiments, A is a nitrogen-, oxygen-, or sulfur-linked aryl, alkyl, cyclic, or heterocyclic group. The A moieties thus described have leaving group characteristics. In embodiments encompassed by the present invention, A is further substituted with an electron contributing moiety. Additionally, B and C are hydrogen, or either B or C is a halogen, amino, or thiol group and the other of B or C is hydrogen; and D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge.

Preferably, A is a substituted N-linked aryl or heterocyclic group, an O-linked aryl or heterocyclic group having the formula —O—Y, or an S-linked aryl or heterocyclic group having the formula —O—Y; both B and C are hydrogen, or either B or C is a halogen, amino, or thiol group and the other of B or C is hydrogen; and D is a primary alcohol or hydrogen. Nonlimiting preferred examples of A are set forth in Table 1, where each R is H or an electron-contributing moiety and Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl.

TABLE 1

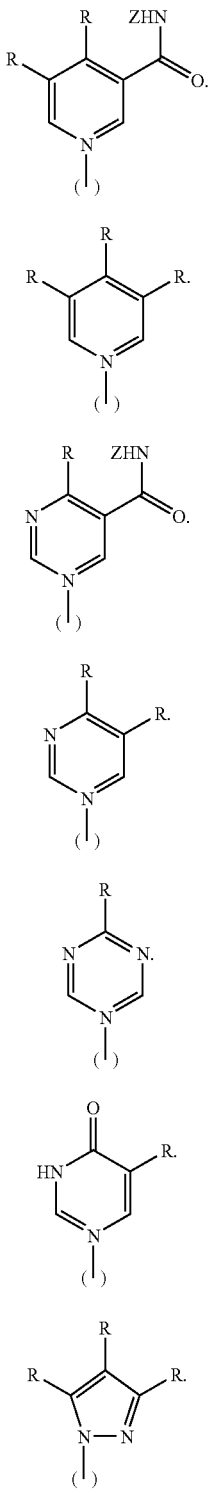

TABLE 1-continued

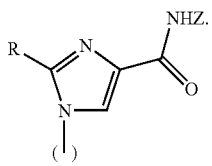

viii.

More preferably, A is a substituted nicotinamide group (Table 1, i, where Z is H), a substituted pyrazolo group (Table 1, vii), or a substituted 3-carboxamid-imidazolo group (Table 1, viii, where Z is H). Additionally, preferably, both B and C are hydrogen, or either B or C is a halogen, amino, or thiol group and the other of B or C is hydrogen; and D is a primary alcohol or hydrogen.

Without being bound to any particular mechanism, it is believed that the electron-contributing moiety on A stabilizes the compounds of the invention such that they are less susceptible to hydrolysis from the rest of the compound. For example, the compound β-1'-5-methyl-nicotinamide-2'-deoxyribose (established as an effective inhibitor of CD38 in the Example) was compared with β-1'-nicotinamide-2'-deoxyribose in its ability to resist solution hydrolysis. The measured rate constant for solution hydrolysis (10 mM potassium phosphate, pH 6.5, 25° C.) of β-1'-nicotinamide-2'-deoxyribose was $9.6 \times 10^{-5}$ $s^{-1}$ whereas the rate of solution hydrolysis of β-1'-5-methyl-nicotinamide-2'-deoxyribose was measured at $1.5 \times 10^{-5}$ $s^{-1}$, demonstrating that the methyl group on the nicotinamide-2'-deoxyriboside caused a decrease in the rate of hydrolysis by a factor of 6. This difference in chemical stability means that β-1'-nicotinamide-2'-deoxyribose is 50% depleted from solution in 2 hours, whereas β-1'-5-methyl-nicotinamide-2'-deoxyribose is not hydrolyzed by 50% until 12 hours. This improved chemical stability improves the value of the compound, since it is available for action for longer periods of time in biological systems due to resistance to hydrolytic breakdown.

The skilled artisan could envision many electron-contributing moieties that would be expected to serve this stabilizing function. Nonlimiting examples of suitable electron contributing moieties are methyl, ethyl, O-methyl, amino, $NMe_2$, hydroxyl, $CMe_3$, aryl and alkyl groups. Preferably, the electron-contributing moiety is a methyl, ethyl, O-methyl, amino group. In the most preferred embodiments, the electron-contributing moiety is a methyl group.

It is also preferred that, in addition to the electron-contributing moiety, the A group also comprises a carboxamid ($CONH_2$) group, as in nicotinamide, as it is believed that the carboxamid group improves the ability of the compound to be inhibitory to ADP-ribosyl cyclases, ADP-ribosyl hydrolases, ADP-ribosyl transferases, and/or NAD-dependent deacetylases, such as CD38.

In some embodiments, A has two or more electron contributing moieties.

Some preferred examples of the compounds of the invention are provided as compounds I, II, and III below.

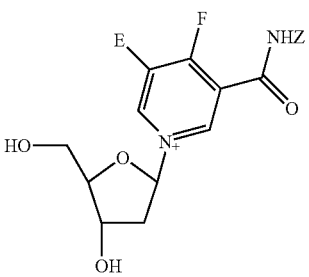

I wherein Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl; E and F are independently H, $CH_3$, $OCH_3$, $CH_2CH_3$, $NH_2$, OH, NHCOH, $NHCOCH_3$, $N(CH_3)_2$, $C(CH_3)_2$, an aryl or a C3–C10 alkyl, preferably provided that, when either of E or F is H, the other of E or F is not H;

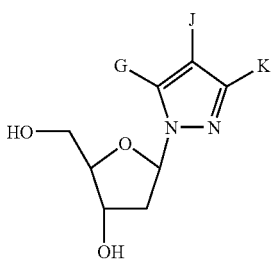

II wherein G, J or K is CONHZ, Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl, and the other two of G, J and K is independently $CH_3$, $OCH_3$, $CH_2CH_3$, $NH_2$, OH, NHCOH, $NHCOCH_3$;

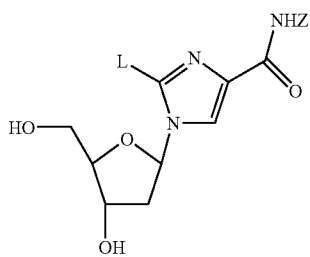

III wherein Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl; and L is $CH_3$, $OCH_3$, $CH_2CH_3$, $NH_2$, OH, NHCOH, $NHCOCH_3$.

In more preferred embodiments, the compound is formula I above, wherein E and F are independently H, $CH_3$, $OCH_3$, or OH, preferably provided that, when either of E or F is H, the other of E or F is not H.

In even more preferred embodiments, the compound is β-1'-5-methyl-nicotinamide-2'-deoxyribose, β-D-1'-5-methyl-nicotinamide-2'-deoxyribofuranoside, β-1'-4,5-dimethyl-nicotinamide-2'-deoxyribose or β-D-1'-4,5-dimethyl-nicotinamide-2'-deoxyribofuranoside.

In the most preferred embodiment, the compound is β-1'-5-methyl-nicotinamide-2'-deoxyribose.

Preferably, the compounds of the present invention are inhibitors of ADP-ribosyl cyclases, ADP-ribosyl hydrolases, ADP-ribosyl transferases, and/or NAD-dependent deacetylases, such as CD38. See Example.

Even though it is preferred that the compounds are inhibitors of ADP-ribosyl cyclases, ADP-ribosyl hydrolases, ADP-ribosyl transferases, and/or NAD-dependent deacetylases, the forms of the compounds that are not inhibitors are also useful, for example as a negative control in studies of the effectiveness of the inhibitor for therapeutic purposes.

Methods for determining the inhibitory activity of any particular compound are routine. Inhibitory activity of the compounds disclosed herein can be determined by standard assays known in the art. For example, the enzyme may be incubated with the inhibitor and a substrate of the enzyme, and absorbance then may be monitored, as described below. Additionally, the enzyme may be incubated with a radioactive inhibitor, and radiochemical measurements of reaction rates may be taken, as described below. Slow-onset inhibitor binding may be determined using methods such as those described in Merkler et al., 1990.

Molecules of the novel class of mechanism-based inhibitors disclosed herein accomplish mechanism-based trapping at the catalytic site of their target enzymes. The inhibitor is designed to react rapidly to form a covalent intermediate that cannot cyclize and that is relatively stable to hydrolysis, thereby trapping the enzyme in a catalytically-inactive form. For example, as elaborated in the Example, the novel inhibitor β-D-1'-5-methyl-nicotinamide-2'-deoxyribose acts as a reversible competitive inhibitor ($K_i$=4.0 μM) of CD38, and is followed by slow-onset inactivation of the enzyme. Inactivated enzyme is covalently modified by the deoxyriboside. Active CD38 is slowly regenerated by hydrolysis in the absence of added substrates, and is rapidly regenerated in the presence of excess nicotinamide. These properties of inhibitor action give rise to an effective inhibition constant of 12.5 nM. This novel class of mechanism based inhibitors has potential for the regulation of cyclic ADP-ribose levels through CD38, and provides new tools for investigating the various pathways in which ADP-ribosyl transferases, cyclases, and hydrolases, and NAD-dependent deacetylases have been implicated.

The compounds of the present invention are useful both in free form and in the form of salts. The term "pharmaceutically acceptable salts" is intended to apply to non-toxic salts derived from inorganic or organic acids and includes, for example, salts derived from the following acids: hydrochloric, sulfuric, phosphoric, acetic, lactic, fumaric, succinic, tartaric, gluconic, citric, methanesulfonic, and p-toluenesulfonic acids.

Also provided are compounds that are the tautomers, pharmaceutically-acceptable salts, esters, and pro-drugs of the inhibitor compounds disclosed herein.

The biological availability of the compounds of the invention can be enhanced by conversion into a pro-drug form. Such a pro-drug can have improved lipophilicity relative to the unconverted compound, and this can result in enhanced membrane permeability. One particularly useful form of pro-drug is an ester derivative. Its utility relies upon the action of one or more of the ubiquitous intracellular lipases to catalyse the hydrolysis of ester groups, to release the active compound at or near its site of action. In one form of pro-drug, one or more hydroxy groups in the compound can be O-acylated, to make an acylate derivative.

Pro-drug forms of a 5-phosphate ester derivative of compounds of the compounds of the present invention can also be made. These may be particularly useful, since the anionic nature of the 5-phosphate may limit its ability to cross cellular membranes. Conveniently, such a 5-phosphate derivative can be converted to an uncharged bis(acyloxymethyl) ester derivative. The utility of such a pro-drug relies upon the action of one or more of the ubiquitous intracellular lipases to catalyse the hydrolysis of ester groups, releasing a molecule of formaldehyde and a compound of the present invention at or near its site of action. Specific examples of the utility of, and general methods for making, such acyloxymethyl ester pro-drug forms of phosphorylated carbohydrate derivatives have been described (Kang et al., 1998; Jiang et al., 1998; Li et al., 1997; Kruppa et al., 1997).

In another aspect, the present invention provides a pharmaceutical composition, comprising a pharmaceutically effective amount of an inhibitor compound of the first aspect of the invention. The inhibitor compound may be chosen from any of those described above. Preferably, the pharmaceutical composition comprises an inhibitor compound chosen from the preferred compounds described above.

In the pharmaceutical composition of the present invention, the pharmaceutically-acceptable carrier must be "acceptable" in the sense of being compatible with the other ingredients of the composition, and not deleterious to the recipient thereof. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may be conveniently presented in unit dosage.

The formulations of the present invention may be prepared by methods well-known in the pharmaceutical art. For example, the inhibitor compound may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the inhibitor composition of the present invention to a subject to treat a disease or condition associated with an ADP-ribosyl transferase, ADP-ribosyl cyclase, ADP-ribosyl hydrolase, or NAD-dependent deacetylase enzyme, including any of those described above. The inhibitor compound is provided in an amount that is effective to treat a disease or condition associated with an ADP-ribosyl transferase, ADP-ribosyl cyclase, ADP-ribosyl hydrolase, or NAD-dependent deacetylase enzyme in the subject. That amount may be readily determined by the skilled artisan, as described above.

According to another aspect of the present invention, there is provided a method for inhibiting an ADP-ribosyl transferase, ADP-ribosyl cyclase, ADP-ribosyl hydrolase, or NAD-dependent deacetylase enzyme. As used herein, "ADP-ribosyl transferase" refers to those enzymes which catalyze the transfer of ADP-ribose (adenosine 5"-diphospho-5'-α-D-ribose) from NAD$^+$ (nicotinamide adenine dinucleotide) to acceptor groups that are chemically reactive as nucleophiles, as well as enzymes that share catalytic site homology with such enzymes. The acceptor groups include the nucleophilic groups of proteins, nucleic acids, sugars, and lipids. Biologically reactive nucleophiles also include other metabolites containing carboxyl groups, amino groups, guanidinium groups, thiol groups, and nitrogens of aromatic or aliphatic compounds, as well as other groups chemically recognized as having nucleophilic character. The ADP-ribosyl transferase family of enzymes produces ADP-ribosylated proteins, ADP-ribosylated nucleic acids, ADP-ribosylated sugars, sugar polymers in homo- or heteropolymeric forms, glycoproteins, ADP-ribosylated lipids, and ADP-ribosylated compounds of cellular metabolism. Compounds of cellular metabolism include carboxylic acids, sugars, amino acids, lipids, nucleotides, nucleosides, vitamins, and intermediates in the biochemical pathways that synthesize these compounds of cellular metabolism.

As used herein, "ADP-ribosyl cyclase" includes those enzymes that catalyze the conversion of NAD$^+$ to ADP-ribose (adenosine 5"-diphospho-5'-α-D-ribose), in which reaction a chemical bond between carbon 1' of the α-D-ribose group of NAD$^+$ (nicotinamide adenine dinucleotide) is transferred to any nucleophilic acceptor group within the same ADP-ribose molecule, thereby forming a cyclic ring system not existing in the parent molecule of NAD$^+$. Also included are enzymes that share catalytic site homology with such ADP-ribosyl cyclase enzymes. Nucleophilic acceptor groups include nitrogen and oxygen groups of the parent NAD$^+$ molecule (e.g., the structure of cyclic-ADP-ribose, in which the carbon 1' of the α-D-ribose group of NAD$^+$ is cyclized to nitrogen 1' of the adenine ring to form a new cyclic ring).

Additionally, as used herein, "ADP-ribosyl hydrolase" refers to those enzymes that catalyze the transfer of ADP-ribose (adenosine 5"-diphospho-5'-α-D-ribose) from NAD$^+$ (nicotinamide adenine dinucleotide) in the formation of ADP-ribose or cyclic-ADP-ribose. "ADP-ribosyl hydrolase", as used herein, also includes enzymes that catalyze the removal of ADP-ribose, in a hydrolytic reaction, from the ADP-ribosylated groups that are chemically reactive as nucleophiles, defined above. Also included are enzymes that share catalytic site homology with such ADP-ribosyl hydrolase enzymes. ADP-ribosylated groups that are chemically reactive as nucleophiles include the groups of ADP-ribosylated-proteins, ADP-ribosylated-nucleic acids, ADP-ribosylated-sugars, and ADP-ribosylated-lipids from the covalent ADP-ribose. Biologically reactive groups removed from ADP-ribose by hydrolysis may also include biological metabolites containing ADP-ribosylated-carboxyl groups, ADP-ribosylated-amino groups, ADP-ribosylated-guanidinium groups, ADP-ribosylated-thiol groups, ADP-ribosylated-nitrogens of aromatic or aliphatic compounds, and other ADP-ribosylated groups chemically recognized as having nucleophilic character. This family of hydrolases regenerates proteins from ADP-ribosylated proteins, nucleic acids from ADP-ribosylated nucleic acids, sugars from ADP-ribosylated sugars, sugar polymers in homo- or heteropolymeric forms from their ADP-ribosylated states, and glycoproteins from ADP-ribosylated glycoproteins, lipids from ADP-ribosylated lipids, and removes ADP-ribose from ADP-ribosylated compounds of cellular metabolism. Compounds of cellular metabolism include carboxylic acids, sugars, amino acids, lipids, nucleotides, nucleosides, vitamins, and intermediates in the biochemical pathways that synthesize these biological metabolites.

Examples of ADP-ribosyl transferases, cyclases, and hydrolases, and NAD-dependent deacetylases include, without limitation, NAD-dependent deacetylases involved in the regulation of gene expression (e.g., SIR family enzymes and their homologues, human CD38, the human ADP-ribosyl cyclase, invertebrate and plant ADP-ribosyl cyclases [e.g., *Aplysia californica* ADP ribosyl-cyclase], and human bone stromal cell antigen [humBST1]). Preferably, the enzyme of the present invention is CD38.

The method for inhibiting an ADP-ribosyl transferase, ADP-ribosyl cyclase, ADP-ribosyl hydrolase, or NAD-dependent deacetylase comprises contacting an ADP-ribosyl transferase, ADP-ribosyl cyclase, ADP-ribosyl hydrolase, or NAD-dependent deacetylase enzyme with one of the previously described inhibitor compounds or their pharmaceutically-acceptable salts in an amount effective to inhibit the enzyme. The ADP-ribosyl transferase, ADP-ribosyl cyclase, ADP-ribosyl hydrolase, or NAD-dependent deacetylase enzyme may include any of those described above (e.g., ADP-ribosyl-transferases involved in the regulation of gene expression (e.g., SIR family enzymes and their homologues), human CD38, the human ADP-ribosyl cyclase, invertebrate and plant ADP-ribosyl cyclases (e.g., *Aplysia californica* ADP ribosyl-cyclase), and human bone stromal cell antigen (humBST1)). In a preferred embodiment, the enzyme is CD38. Preferably, the inhibitor is one of the preferred inhibitors previously described, in a pharmaceutical composition.

As used herein, an "amount effective to inhibit the enzyme" refers to an amount that disables, disrupts, or inactivates the function of the enzyme. Inhibitor compounds contemplated for the inhibition of ADP-ribosyl transferase, ADP-ribosyl cyclase, ADP-ribosyl hydrolase, or NAD-dependent deacetylase enzymes may form a combination of enzyme and inhibitor, thereby generating complexes that reduce the catalytic function of the enzyme.

The inhibitor compound of the present invention, or a pharmaceutically-acceptable salt thereof, may be contacted with the enzyme either in vivo or in vitro, using techniques well known to one of skill in the art. Where contacting is effected in vitro, the inhibitor compound may be used as tools for investigating the pathways in which ADP-ribosyl transferase, ADP-ribosyl cyclase, ADP-ribosyl hydrolase, or NAD-dependent deacetylase enzymes are involved. Where contacting is effected in vivo, the inhibitor compound may be used to treat a disease or condition in which it is desirable to decrease the activity of an ADP-ribosyl transferase, ADP-ribosyl cyclase, ADP-ribosyl hydrolase, or NAD-dependent deacetylase enzyme.

Accordingly, the present invention further provides methods for treating a disease or condition that is directly or indirectly associated with an ADP-ribosyl transferase, ADP-ribosyl cyclase, ADP-ribosyl hydrolase, or NAD-dependent deacetylase enzyme in a subject in need of treatment thereof. These methods comprise administering to the subject any one of the previously described inhibitor compounds, or a pharmaceutically-acceptable salt thereof, in an amount effective to treat the disease or condition. As used herein, a "subject" is a mammal, including, without limitation, a cow, dog, human, monkey, mouse, pig, or rat, as described above. Preferably, the subject is a human. The ADP-ribosyl transferase, ADP-ribosyl cyclase, ADP-ribosyl hydrolase, or NAD-dependent deacetylase enzyme may include any of those described above (e.g., NAD-dependent deacetylases involved in the regulation of gene expression [e.g., SIR family enzymes and their homologues], human CD38, the human ADP-ribosyl cyclase, invertebrate and plant ADP-ribosyl cyclases [e.g., *Aplysia californica* ADP ribosyl-cyclase], and human bone stromal cell antigen [humBST1]). In one embodiment of the present invention, the enzyme is CD38.

As used herein, "disease" refers to any deviation from, or interruption of, the normal structure or function of any part, organ, or system (or combination thereof) of the body that presents an abnormal or pathologic body state. As further used herein, "condition" refers to any state of physical or mental abnormality. Furthermore, as used herein, "a disease or condition associated with an ADP-ribosyl transferase, ADP-ribosyl cyclase, ADP-ribosyl hydrolase, or NAD-dependent deacetylase enzyme" includes a disease or condition wherein an ADP-ribosyl transferase, ADP-ribosyl cyclase, ADP-ribosyl hydrolase, or NAD-dependent deacetylase enzyme contributes to (either directly or indirectly), or is responsible for, the pathophysiology of the disease or condition, or in which it is desirable to decrease the activity of an ADP-ribosyl transferase, ADP-ribosyl cyclase, ADP-ribosyl hydrolase, or NAD-dependent deacetylase enzyme, or in which it is desirable to regulate the level of cADPR.

Inhibition of cADPR-stimulated calcium release is expected to have significant effects on calcium-mediated signaling pathways in many cells and tissues. Accordingly, in the method of the present invention, the disease or condition associated with an ADP-ribosyl transferase, ADP-ribosyl cyclase, ADP-ribosyl hydrolase, or NAD-dependent deacetylase enzyme may include any disease or condition associated with a defect or deficiency in the transmembrane flux of calcium ($Ca^{2+}$) ions into or out of cells, particularly vascular smooth muscle cells, cardiac muscle cells, and cells of the nervous system. Examples of such diseases may include, without limitation, angina (e.g., angina pectoris, chronic stable angina, and vasospastic angina), arrhythmias, atrial fibrillation, hypertension, paroxysmal supraventricular tachycardia, acute disseminated encephalomyelitis (ADEM), acute transverse myelitis, acute viral encephalitis, adrenoleukodystrophy (ALD), adrenomyeloneuropathy, AIDS-vacuolar myelopathy, experimental autoimmune encephalomyelitis (EAE), experimental autoimmune neuritis (EAN), HTLV-associated myelopathy, Leber's hereditary optic atrophy, multiple sclerosis (MS), progressive multifocal leukoencephalopathy (PML), subacute sclerosing panencephalitis, and tropical spastic paraparesis.

In mammals, CD38 and CADPR have been implicated in the regulation of cellular processes, including insulin release (Okamoto et al., 1999), lymphocyte activation (Mehta et al., 1996; Cockayne et al., 1998), bone homeostasis (Sun et al., 1999), neutrophil activation in response to acute bacterial (or pathogen) infection with possible roles in inflammation and inflammatory diseases (Partida-Sanchez et al., 2001; Normark et al., 2001), and synaptic plasticity (Reyes-Harde et al., 1999). Accordingly, the disease or condition associated with an ADP-ribosyl transferase, ADP-ribosyl cyclase, ADP-ribosyl hydrolase, or NAD-dependent deacetylase enzyme also may include diseases or conditions associated with insulin release (e.g., diabetes), lymphocyte activation, bone homeostasis, and synaptic plasticity.

In these methods, the inhibitor compound may be chosen from any of those previously described. Preferably, the inhibitor compound is in a pharmaceutical composition and is one of the preferred compounds previously described.

In the method of the present invention, an inhibitor compound, as disclosed herein, is administered to a subject who has a disease or condition associated with an ADP-ribosyl transferase, ADP-ribosyl cyclase, ADP-ribosyl hydrolase, or NAD-dependent deacetylase enzyme, in an amount effective to treat the disease or condition in the subject. As used herein, the phrase "effective to treat the disease or condition" means effective to ameliorate or minimize the clinical impairment or symptoms resulting from the disease or condition associated with an ADP-ribosyl transferase, ADP-ribosyl cyclase, ADP-ribosyl hydrolase, or NAD-dependent deacetylase enzyme. For example, where the disease or condition is hypertension, the clinical impairment or symptoms of the disease or condition may be ameliorated or minimized by decreasing systolic and/or diastolic blood pressure, and thereby minimizing dizziness, flushed face, fatigue, headache, epistaxis, nervousness, and other symptoms associated with hypertension, particularly severe hypertension.

The amount of inhibitor compound effective to treat a disease or condition associated with an ADP-ribosyl transferase, ADP-ribosyl cyclase, ADP-ribosyl hydrolase, or NAD-dependent deacetylase enzyme in a subject in need of treatment thereof will vary depending on the particular factors of each case, including the type of disease or condition associated with an ADP-ribosyl transferase, ADP-ribosyl cyclase, ADP-ribosyl hydrolase, or NAD-dependent deacetylase enzyme, the subject's weight, the severity of the subject's condition, and the method of administration. Typically, the dosage for an adult human will range from less than 1 mg to 1000 mg (preferably, 0.1 mg to 100 mg). Nevertheless, requisite amounts can be readily determined by the skilled artisan.

It is within the confines of the present invention that the inhibitor compounds disclosed herein may be administered to a subject who is already receiving an inhibitor of the ryanodine receptor or an antagonist that binds the ryanodine receptor. The inhibitor compounds of the present invention, when contacted with an ADP-ribosyl transferase, cyclase, or hydrolase, or an NAD-dependent deacetylase enzymes described herein, result in a decrease in cADPR concentration. It is expected that this decrease would prevent CADPR from competing against antagonists or inhibitors binding at the same site on the ryanodine receptors.

In these methods, the inhibitor compound may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump. Preferably, the inhibitor compound of the present invention is administered orally.

For oral administration, the inhibitor compound may be formulated in solid or liquid preparations, e.g., capsules, tablets, powders, granules, dispersions, solutions, and suspensions. Such preparations are well known in the art as are other oral dosage forms not listed here. In a preferred embodiment, the inhibitor compounds of the invention are tableted with conventional tablet bases, such as lactose, sucrose, mannitol, and corn starch, together with a binder, a disintegration agent, and a lubricant. These excipients are well known in the art. The formulation may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate. Other components, such as coloring agents and flavoring agents, also may be included. Liquid forms for use in the invention include carriers, such as water and ethanol, with or without other agents, such as a pharmaceutically-acceptable surfactant or suspending agent.

For parenteral administration (i.e., administration by injection through a route other than the alimentary canal), the inhibitor compound may be combined with a sterile aqueous solution which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampules or vials. The formulation may be delivered by any mode of injection, including, without limitation, epifascial, intracapsular, intracutaneous, intradermal, intramuscular, intraorbital, intraperitoneal, intraspinal, intrasternal, intravascular, intravenous, parenchymatous, or subcutaneous.

For transdermal administration, the inhibitor compound may be combined with skin penetration enhancers, such as propylene glycol, polyethylene glycol, isopropanol, ethanol, oleic acid, N-methylpyrrolidone, and the like, which increase the permeability of the skin to the inhibitor compound, and permit the inhibitor compound to penetrate through the skin and into the bloodstream. The inhibitor compound/enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The inhibitor compound may be administered transdermally, at or near the site on the subject where the disease or condition is localized. Alternatively, the inhibitor compound may be administered transdermally at a site other than the affected area, in order to achieve systemic administration.

The inhibitor compound of the present invention also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the inhibitor compound.

In another aspect, the present invention provides a method of preparing the inhibitor compounds of the first aspect of the invention. The method may include one or more of the methods disclosed herein, as well as other methods that will be apparent to those of skill in the art. The method of preparing the inhibitor compounds of the present invention may involve a reaction in the presence of silver, as an adaptation of several $Hg^{2+}$ couplings and chlorosugars to form nucleosides. In general, the method will comprise the following steps: (a) contacting a deoxyribose sugar (e.g., β-3,5-bis-parachlorobenzoyl-1-pyridyl-2-deoxyribose), or a mixture containing a deoxyribose sugar and a base (e.g., 3,5-bis-parachlorobenzoyl-1-α-chloro-2-deoxyribose and nicotinamide), with a mixture containing both a silver compound (e.g., $AgSbF_6$) and the compound to be reacted with the deoxyribose sugar (e.g., pyridine or nicotinamide), thereby forming a reaction mixture; (b) redissolving the reaction mixture in MeOH; (c) adding $NH_4Cl$ to the reaction mixture; (d) filtering the reaction mixture to remove precipitated residual silver; (e) treating the reaction mixture with $NH_3$ in MeOH; (f) adding water to the reaction mixture; and (g) purifying the reaction mixture (e.g., with HPLC). See Example for methods for preparation of particular compounds.

Preferred embodiments of the invention are described in the following Example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE

Studies with Mechanism-Based Inhibitors of CD38.

EXAMPLE SUMMARY

The soluble domain of human CD38 catalyzes the conversion of $NAD^+$ to cyclic-ADP-ribose and to ADP-ribose via a common covalent intermediate (Sauve et al., 2000). Here we establish that mechanism-based inhibitors can be produced by chemical stabilization of this intermediate. The compounds nicotinamide-2'-deoxyriboside (1), 5-methyl-nicotinamide-2'-deoxyriboside (2) and pyridyl-2'-deoxyriboside (3) (FIG. 1) were synthesized and evaluated as inhibitors for human CD38. The nicotinamide derivatives 1 and 2 were inhibitors of the enzyme as determined by competitive behavior in CD38 catalyzed conversion of nicotinamide guanine dinucleotide ($NGD^+$) to cyclic-GDP-ribose. The $K_i$ values for competitive inhibition were 1.2 μM and 4.0 μM for 1 and 2 respectively. Slow-onset characteristics of reaction progress curves indicated a second higher affinity state of these two inhibitors. Inhibitor off-rates were slow with rate constants $k_{off}$ of $1.5 \times 10^{-5}$ $s^{-1}$ for 1 and $2.5 \times 10^{-5}$ $s^{-1}$ for 2. Apparent dissociation constants $K_{i(total)}$ for 1 and 2 were calculated to be 4.5 and 12.5 nM respectively. The similar values for $k_{off}$ are consistent with the hydrolysis of common enzymatic intermediates formed by the reaction of 1 and 2 with the enzyme. Both form covalently attached deoxy-ribose groups to the catalytic site nucleophile. Chemical evidence for this intermediate is the ability of nicotinamide to rescue enzyme activity after inactivation by either 1 or 2. A covalent intermediate is also indicated by the ability of CD38 to catalyze base exchange, as observed by converion of 2 to 1 in the presence of nicotinamide. The deoxynucleosides 1 and 2 demonstrate that the chemical determinants for mechanism-based inhibition of CD38 can be satisfied by nucleosides that lack the 5'-phosphate, the adenylate group and the 2'-hydroxyl moiety. In addition, these compounds reveal the mechanism of CD38 catalysis to proceed by the formation of a covalent intermediate during normal catalytic turnover with faster substrates. The covalent 2'-deoxynucleoside inactivators of CD38 are powerful inhibitors by acting as good substrates for formation of the covalent intermediate but are poor leaving groups from the intermediate complex because hydrolytic assistance of the 2'-hydroxyl group is lacking. The removal of the adenylate nucleophile required for the cyclization reaction provides slow hydrolysis as the only exit from the covalent complex.

Methods

Reagents for chemical synthesis were obtained from commercial vendors and were used as received. The synthesis of 1-chloro-di-p-chloro-benzoyl-2-deoxyriboside (4), was synthesized as reported (Fox et al., 1961). This sugar could be stored with a $P_2O_5$ sidearm for desiccation and stored at −78° C. [2'-$^3$H]deoxyuridine was obtained from ARC in 5 mCi quantity and used as received. Thymidine phosphorylase and alkaline phosphatase was obtained from Sigma. NMR data was obtained on a Bruker DRX-300 instrument.

Synthesis of β-3,5-p-chlorobenzoyl-1-nicotinamide-2-deoxyriboside. 100 mg (0.3 mmol) of 4 was added to a flame-dried flask containing 90 mg (0.8 mmol) nicotinamide. To a second flask, 20 mg (0.2 mmol) nicotinamide and 100 mg $AgSbF_6$ (0.3 mmol) was added, with 5 mL acetonitrile to dissolve the salt. The silver solution was cooled to 0° C. with ice and then added rapidly by syringe to the flask containing the base and sugar. The solution was stirred chilled in an ice bath and a grayish precipitate formed. The reaction was stirred for 2 hours chilled and then warmed to room temperature and stirred an additional 2 hours. The reaction mixture was evaporated, the residue redissolved in MeOH and filtered through Celite. The filtrate was evaporated. The material was determined by NMR to contain the desired product in a mixture of stereoisomers (9:1 β:α) in a yield of 85%. $^1$H NMR, $d_3$-MeOD δ: (9.54 s, 1H), (9.25, s, 1H), (8.93, d, 1H), (8.2, m, 1H), (8.0–7.8, m, 4H), (7.6–7.3, m, 4H), (6.79, t, 1H), (5.77, m, 1H), (5.01, m, 1H), (4.99–4.4, m, 3H), (3.44, m, 1H), (2.9, m, 1H).

Synthesis of β-nicotinamide-2'-deoxyriboside (1). The above material was subjected to deprotection without further purification by treatment with 5 mL 2 M $NH_3$ in MeOH at −20° C. This solution was reacted for 8 hours at −20° C. TLC was used to monitor the reaction. The MeOH and $NH_3$ were evaporated at reduced pressure and the residue redissolved in 300 μL of methanol. 1 mL of water was then added. A gummy precipitate was removed by centrifugation and the aqueous phase was purified by HPLC to yield pure α and β deprotected isomers of 1. These isomers were analyzed by $^1$H NMR. Inhibitor solutions were measured at 266 nm for absorbance (concentration) and frozen upon isolation by HPLC and placed at −78° C. for later use. $^1$H NMR, $D_2O$, δ: (9.5, s, 1H), (9.18, d, 1H), (8.84, d, 1H), (8.16, t, 1H), (6.56, t, 1H), (4.47, m, 1H), (4.29, m, 1H), (4.5–4.0, m, 2H), (3.0, m, 1H), (2.82, m, 1H). MS: $M^+$=239.

Synthesis of β-3,5-p-chlorobenzoyl-1-5-methyl-nicotinamide-2-deoxyriboside. 100 mg (0.3 mmol) of 4 was added to a flask along with 50 mg (0.4 mmol) 5-methyl-nicotinamide. To this flask was added 2 mL $CH_2Cl_2$, and the flask kept on ice. To a second flask 50 mg (0.4 mmol) 5-methyl-nicotinamide and 2 mL acetonitrile was added. The solution was heated to 50° C. to dissolve the 5-methyl-nicotinamide and subsequently cooled to room temperature. 100 mg $AgSbF_6$ (0.3 mmol) was added and the silver solution cooled to 0° C. with an ice bath. After several minutes on ice the contents of the silver solution were rapidly transferred by syringe to the flask containing the base and sugar. The solution was stirred while chilled by an ice bath and a grayish precipitate formed. The reaction was stirred for 2 hours chilled and then warmed to room temperature and stirred an additional 2 hours. The reaction mixture was evaporated, the residue redissolved in MeOH and filtered through Celite. The filtrate was then evaporated. The material was determined by NMR to be a mixture of stereoisomers in a ratio of 4.2:1 (β:α) in yield of 95%. $^1$H NMR, $CD_3CN$ δ: (9.298, s, 1H), (9.017, s, 1H), (8.804, s,1H), (8.275, d, 2H), (8.04, d, 2H), (7.77, d, 2H), (7.64, d, 2H), (6.78, t, 1H), (5.90, m, 1H), (5.178, m, 1H), (4.99–4.7, m, 2H), (3.44, m, 1H), (3.1, m, 1H). (2.66, s, 3H).

Synthesis of β-5-methyl-nicotinamide-2'-deoxyriboside (2). This material was subjected to deprotection without further purification by addition of 4 mL 2 M $NH_3$ in MeOH added at −20° C. and the reaction permitted to go for 8 hours at −20° C. The MeOH and $NH_3$ were then evaporated at reduced pressure and the residue redissolved in 1 mL of cold water. After trituration with water the suspension was spun to remove precipitate and the aqueous phase purified by HPLC to yield the pure α and β deprotected isomers of 2. These isomers could be analyzed by $^1H$ NMR by rapid evaporation and redissolution in $D_2O$. Inhibitor solutions were measured at 273 nm for absorbance (concentration) and frozen upon isolation by HPLC and placed at −78° C. $^1H$ NMR, $D_2O$, δ:(9.73, s, 1H), (9.43, s, 1H), (9.11, s, 1H), (6.86, t, 2H), (4.64, m, 1H), (4.11, m, 1H), (4.04–3.78, m, 3H), (3.17, m, 1H), (2.96, s, 3H), (2.84, m, 1H).

Synthesis of β-3,5-p-chlorobenzoyl-1-pyridyl-2-deoxyriboside. 50 mg (0.15 mmol) of 4 was added to a flask. To a second flask was added 30 μL pyridine and 50 mg $AgSbF_6$ (0.15 mmol) and 5 mL acetonitrile/$CH_2Cl_2$ (1:4) was added to dissolve the salt. The silver solution was cooled to 0° C. with ice and then added to the flask containing the sugar. The solution was stirred chilled by ice bath and a precipitate was observed to form. The reaction was stirred for 2 hours chilled and then warmed to room temperature overnight. The reaction mixture was evaporated and the residue redissolved in MeOH and filtered through Celite. The filtrate was then evaporated. The material was determined by NMR to be a mixture of stereoisomers (14.3:1, β:α) in yield of 95%. $^1H$ NMR, $CD_3CN$ δ: (9.19, d, 2H), (8.72, t, 1H), (8.27, t, 2H), (8.0–7.8, m, 4H), (7.7–7.5, m, 4H), (6.88, t, 1H), (5.92, m, 1H), (6.78, t, 1H), (5.2, m, 1H), (4.9, m, 1H), (3.4, m, 1H), (3.0, m, 1H).

Synthesis of β-pyridyl-deoxyriboside (3). The protected material above was subjected to deprotection without further purification by addition of 4 mL 2 M $NH_3$ in MeOH added at 0° C. and the reaction permitted to go for 12 hours at 4° C. At the end of this time TLC indicated total consumption of starting material. The MeOH and $NH_3$ were then evaporated at reduced pressure and the residue redissolved in 300 μL of methanol followed by addition of 1 mL of water. After trituration with water the suspension was spun to remove precipitate and the aqueous phase purified by HPLC to yield the pure α and β deprotected isomers. 10.4:1 (β:α). $^1H$ NMR, $D_2O$, δ: (9.17, d, 2H), (8.72, t, 1H), (8.24, t, 2H), (6.66, t, 2H), (4.64, m, 1H), (4.44, dd, 1H), (4.04, dd, 1H), (3.92, dd, 1H), (2.99, m, 1H), (2.74, m, 1H).

Determination of $K_i$ and $k_{on}$ by competitive method. To 1 mL solutions of 50 mM potassium phosphate pH 7.2 and 100 μM $NGD^+$ containing, 50, 25, 12.5, and 6.25 and 0 μM inhibitor 1 was added 2 μL of 7 μM CD38. Reaction progress upon initiation by enzyme addition was monitored by measurement of 295 nm absorbance. The initial slopes were used to determine the $K_i$ value, and all points of the experiment were fit to the equation $A(t)=vt+(b-v)(1-\exp(-kt))/k+A_0$ where k is the observed rate constant, b is the initial rate, v is the final rate and $A_0$ is the initial absorbance was used to evaluate $k_{on}$. A similar procedure was used for inhibitor 2, with concentrations of components given in FIG. 3.

Off-Rate Measurement. 500 nM CD38 in 50 mM potassium phosphate pH 7.2 was incubated with 15 μM inhibitor for 30 min at room temperature. 5 μL of the enzyme inhibitor solution was added to a cuvette containing 1 mL reaction of 50 mM potassium phosphate pH 7.5 containing 300 μM $NGD^+$ pre-chilled to 19° C. Production of $NGD^+$ was determined by monitoring 295 nm absorbance. The absorbance was fit to the equation $A(t)=vt+(b-v)(1-\exp(-kt))/k+A_0$ where A(t) is the absorbance, k is the rate constant of recovery, b is the initial rate, v is the final rate and $A_0$ is the initial absorbance. A control lacking inhibitor but in all other respects identical was also run.

Radiochemical measurement of inhibitor binding. [2'-$^3H$] Nicotinamide deoxyriboside (1) was used to measure binding by the following method. Inhibitor at 9 μM with specific radioactivity of 866 cpm/nmol, was incubated with 1.2 μM CD38 (monomer) in 1 mL 50 mM potassium phosphate (pH 7.5). The reactions were started by enzyme addition and quenched by freezing with a dry ice/acetone bath at 30, 60 90, 120, 250, 500, and 1000 s. Cooled (0° C.) gel filtration columns were used to separate protein with cooled (0° C.) 10 mM potassium phosphate as eluant. The frozen fraction were quickly thawed, applied to these columns and fractions collected in 1 mL volumes over the course of several minutes. Scintillation fluid (9 mL) was then added to each 1 mL fraction and samples counted. A sample lacking enzyme was performed as a blank control as was a sample using the α-[2'-$^3H$]nicotinamide deoxyriboside of equal concentration and specific activity. The observed radioactivity was fit using the equation $A(t)=A_0(1-\exp(-kt))+B$. where $A_0$ is activity at reaction completion, k is the observed pseudo-first order rate constant and B is the activity of the blank.

Activity recovery by addition of nicotinamide. 10 mL CD38 (1 μM) in $K_2PO_4H$ was incubated with 2 (10 μM) for 30 minutes at room temperature and subsequently placed on ice. Ten 1.5 mL solutions of NGD (400 μM) containing 0–100 mM nicotinamide were also prepared. To a two syringe Applied Photophysics spectrophotometer in fluorescence mode was added inhibited enzyme to one syringe and $NGD^+$ solution to the other. Fluorescence was used to monitor cGDPR formation and the total fluorescence curves fit using the activity recovery equation $F(t)=vt+(b-v)(1-\exp(-kt))/k+F_0$ where k is the observed rate constant, b is the initial rate, v is the final rate and $F_0$ is the initial absorbance. The value of k was plotted against the nicotinamide concentration and the points fit to the Michaelis-Menten equation using the program Kaleidagraph.

Base-exchange reaction. 75 μM 2 was incubated with 1 μM CD38 enzyme and varying concentrations of nicotinamide (0–40 mM) in 150 μL volumes. These reactions were run separately in autosampler tubes held at 19° C. in a temperature regulated autosampler and assayed by multiinjection HPLC using 5 mM $K_2PO_4H$ pH 5.0 and 2.5% MeOH as eluant. The quantity of 2 reacted and the quantity of 1 formed versus time was determined by integrations of the peaks for 1 and 2 with comparison to standards. The rate of conversion of 1 to 2 versus nicotinamide concentration was plotted and the points fit to the Michaelis-Menten equation using the program Kaleidagraph.

Results

Synthesis of 2-deoxy-nicotinamide-ribosides. Several deoxy-nucleoside compounds (1–3, FIG. 1) bearing 1'-β-pyridyl substitutions were prepared from the chloro-sugar 4 (Scheme 2). In the sugar-base coupling step a stoichiometric quantity (versus sugar) of $AgSbF_6$ was found to significantly improve stereochemical yield of the β isomer and the overall coupling yield. Standard deprotection protocol in cold methanolic ammonia gave the desired derivatives in mixtures of stereoisomers. Pure α and β stereoisomers were obtained by semipreparative reverse phase HPLC.

Scheme 2

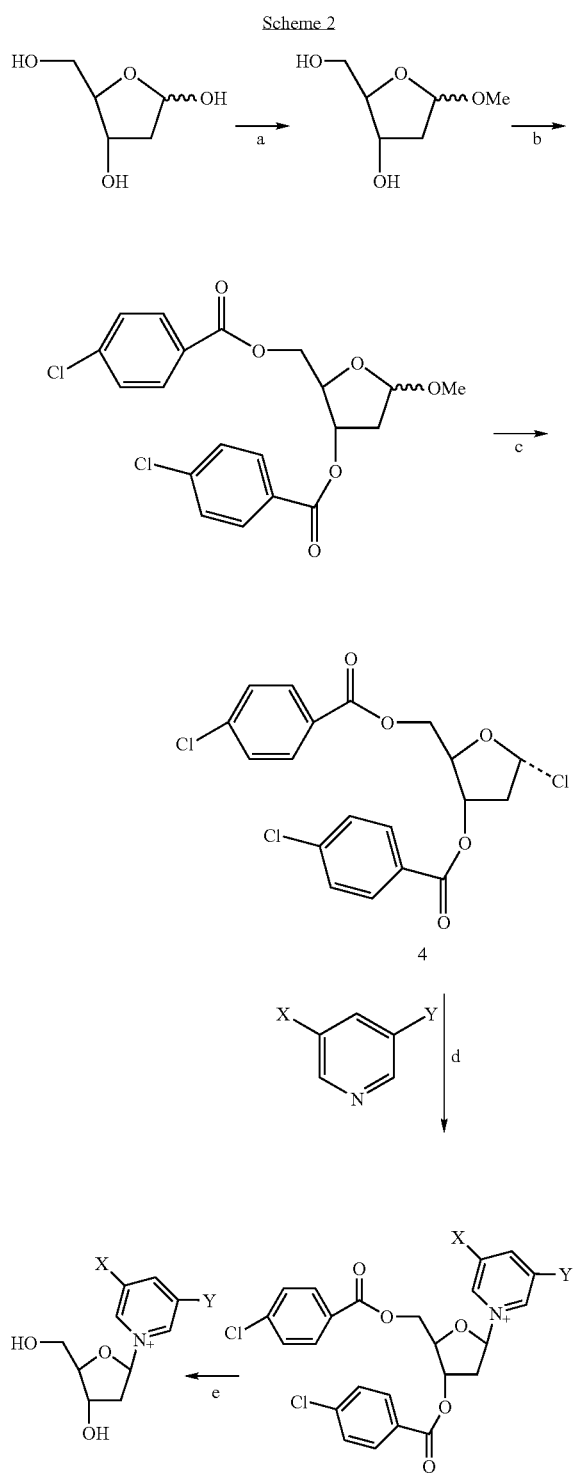

Conditions: a, HCl, MeOH; b, para-chlorobenzoyl chloride, pyridine;
c, AcOH, Et₂O, HCl, 273 K; d, 1.0 eq. AgSbF₆, AcCN, 273 K, e, 2 M NH₃ MeOH Preparation of 2'-³H substituted versions of 1 and 2 were obtained by repeating the syntheses above with [2-³H]2-deoxyribose. This radiolabeled sugar starting material was obtained by digestion of commercially available [2'-³H]2'-deoxyuridine with the enzyme thymidine phosphorylase followed by treatment of the reaction mixture with alkaline phosphatase to form [2-³H]deoxyribose (Scheme 3). The specific radioactivity of the inhibitors was determined to be 866 cpm/nmol.

Scheme 3

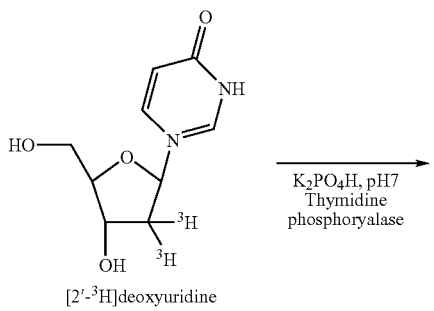

[2'-³H]deoxyuridine

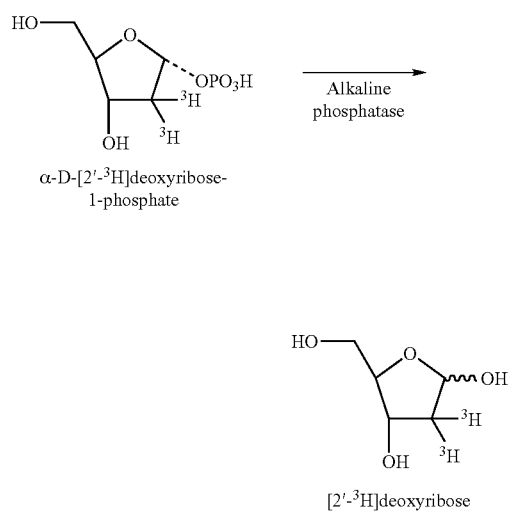

α-D-[2'-³H]deoxyribose-1-phosphate

[2'-³H]deoxyribose

Figure 2:
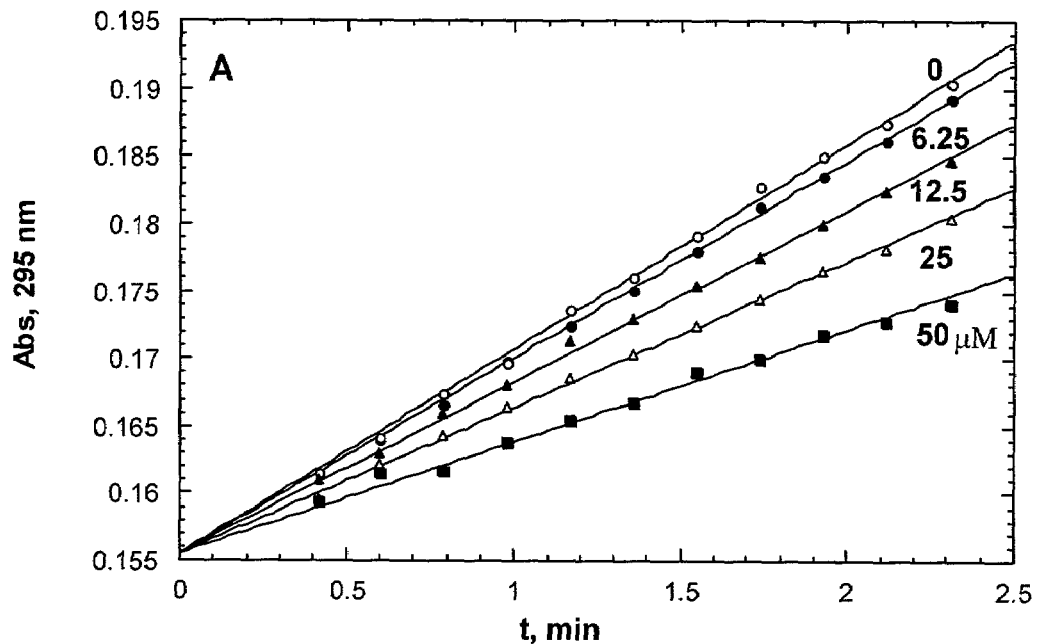
FIG. 2 provides graphs illustrating data measuring time courses of inhibition of CD38 by different concentrations of 1 as assayed by conversion of $NGD^+$ to cGDPR. (100 μM $NGD^+$). Panel A shows the initial rates of reaction of curves from Panel B were fit to the equation for competitive inhibition to determine $K_i$ in Table 2. Panel B shows the extended time courses of two-phase inhibition of CD38 by different concentrations of 1 as assayed by conversion of $NGD^+$ to cGDPR. Inhibitor concentrations are shown. The solid lines represent the best fit to the slow-onset equation given in the text. The rate constant $(k_1)$ for the slow phase derived from these curves is $4.2 \times 10^{-3}$ s$^{-1}$.
Figure 2:
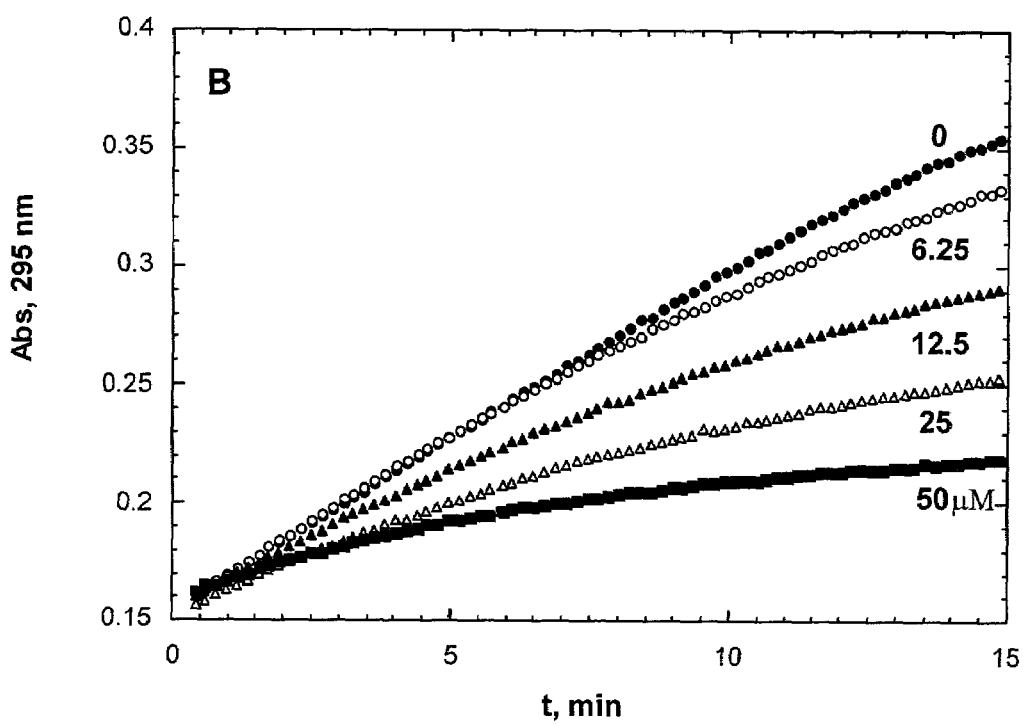
Figure 3:
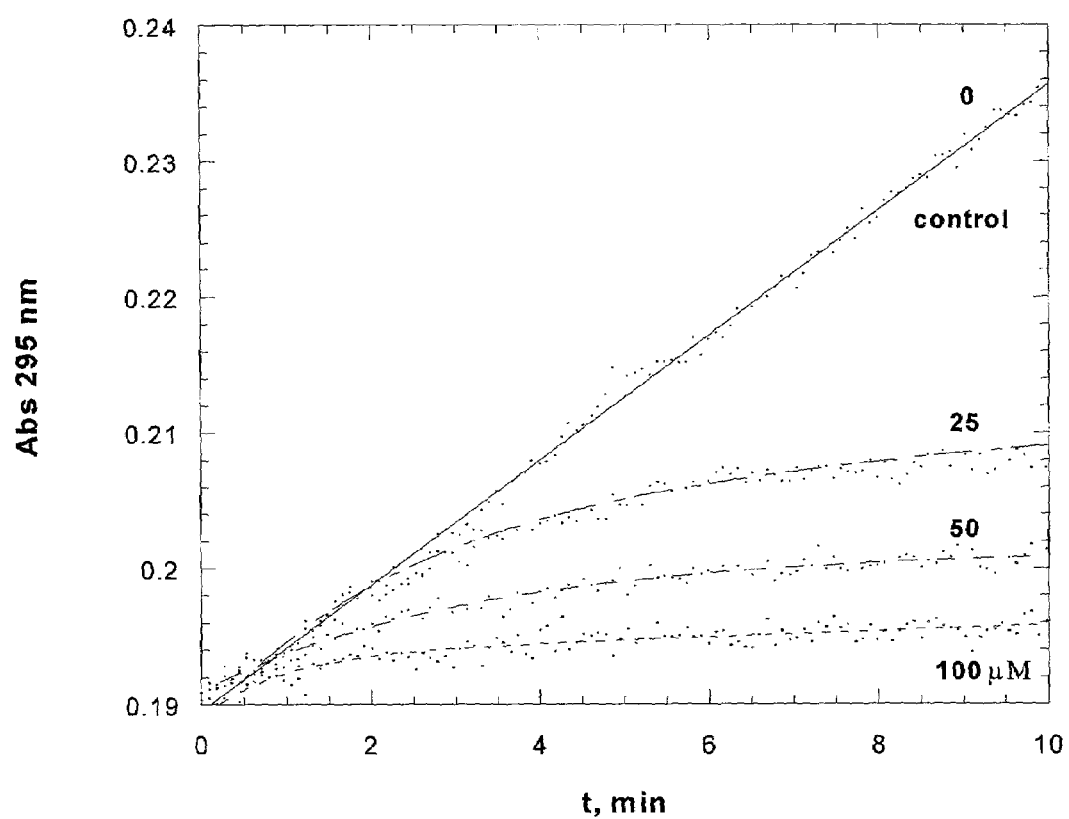
FIG. 3 provides a graph illustrating data measuring time course of two-phase inhibition of CD38 by different concentrations of 1 as assayed by conversion of $NGD^+$ to cGDPR.(40 μM $NGD^+$). Inhibitor concentrations are shown on the right of curves. The solid lines represent the best fit to the slow-onset equation given in the text. The rate constant $(k_{on})$ for the slow phase derived from these curves is $8.3 \times 10^{-3}$ s$^{-1}$. The initial rates from these curves were used to determine $K_i$ (Table 2).

Determination of Competitive Inhibition by Initial Rates: The inhibitors 1–3 were evaluated for inhibition of CD38 enzymatic activity using a spectrophotometric assay. CD38 catalyzes the conversion of NGD⁺ to cyclic-GDP ribose (cGDPR, Scheme 4) and product formation can be monitored by 295 nm absorbance measurement. FIG. 2 shows the behavior of 1 in assays using 100 μM NGD⁺ (50×$K_{m}$, 35) and variable inhibitor concentrations. The initial rates of these reactions (FIG. 2A) demonstrated competitive inhibition of CD38 cyclase activity by 1 with a value for $K_i$ of 1.2 μM±0.3. A similar reaction containing 40 μM NGD⁺ at several concentrations of 2 was also performed (FIG. 3). Initial rates of reaction showed inhibition of CD38 cyclase activity by 2 with a $K_i$ of 4.0±0.5 μM. Reaction mixtures containing 3, the α isomer of 1, or the α isomer of 2 did not inhibit CD38 conversion of NGD⁺ to cGDPR even at millimolar concentrations of these compounds (data not shown).

Scheme 4

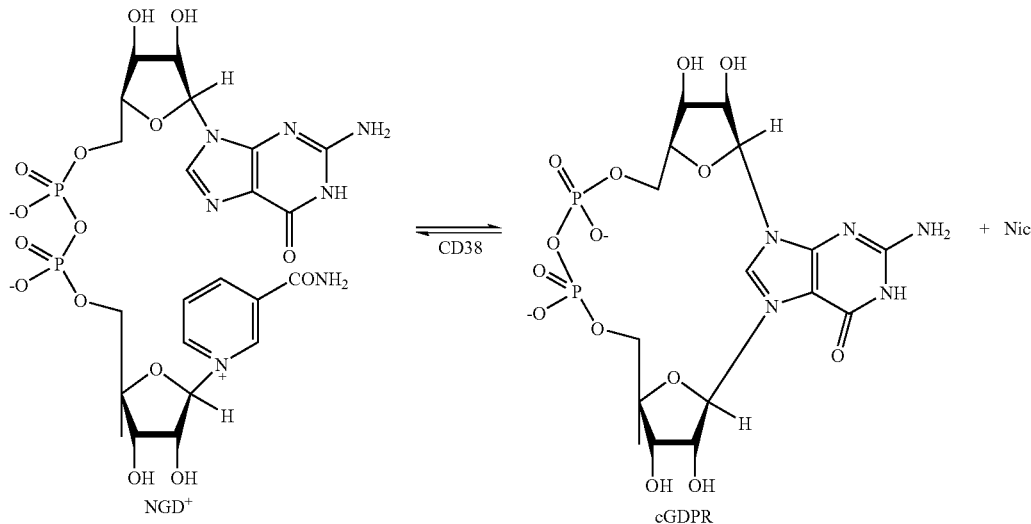

Slow Phase Inhibition. Reaction progress curves of CD38 activity in reaction mixtures containing the inhibitors 1 and 2 showed not only initial rate inhibition but a second phase of slow-onset inhibition indicated by slopes declining monotonically over time as seen in FIG. 2 and FIG. 3. This slow phase was not due to substrate depletion and was attributable to a kinetic process leading to progressive inhibition of the enzyme. The "slow-onset" absorbance curves could be fit using the equation $A_t=v_i t+(v_i-v_f)(1-\exp(-kt))/k+A_0$ where $A_t$ is absorbance, $v_i$ is initial velocity, $v_f$ is final velocity, t is time in s, k is the rate of the slow onset process and $A_0$ is absorbance of the sample at initial time. These fits are shown by the solid lines in FIG. 2 and FIG. 3. The rate constant for the slow phase could be obtained from the average value of k determined from the separate fits. The value of k for 1 was determined to be $0.0042\pm0.001$ s$^{-1}$ and the value of k for 2 was determined to be $0.0083\pm0.002$ s$^{-1}$. The parameter k is defined as $k_{on}$ in Scheme 5.

Scheme 5

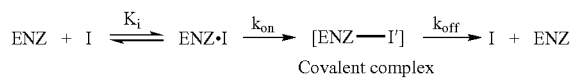

Covalent complex

Figure 4:
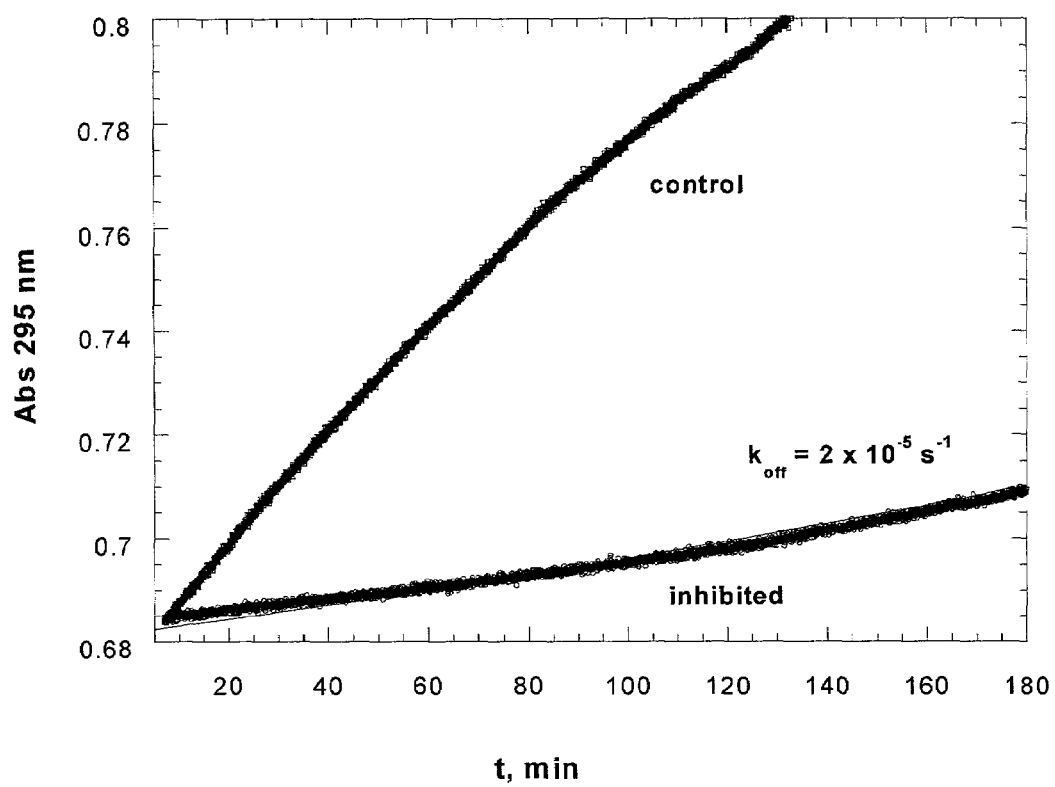
FIG. 4 provides a graph of data from a recovery experiment to measure rate of recovery of CD38 from inhibition by 1 in the presence of excess $NGD^+$. The top curve is a control, of uninhibited enzyme. The bottom curve shows the recovery process as increasing free CD38 generates increasing rates of cGDPR formation. The solid curve represents the best fit to the recovery equation described in the text. The recovery rate determined was $2 \times 10^{-5}$ s$^{-1}$.

Recovery from Inhibition. To fully characterize the inhibition of 1 and 2 against CD38, determinations of the inhibitor off-rates were needed. The inhibitor off-rate provides the final parameter in the equation $k_{off}/k_{on}*K_i=K_{i(total)}$ which is valid for the kinetic scheme of slow-onset inhibition shown in Scheme 5. This rate was obtained by a recovery protocol in which inhibited CD38 enzyme (by either 1 or 2) was added to a 200 μM solution of NGD$^+$. The solution 295 nm absorbance is monitored spectrophotometrically to assay conversion of NGD$^+$ to cGDPR as a consequence of regain of CD38 catlytic activity. Typical curves obtained are shown in FIG. 4. The top curve shows product formation a control reaction using uninhibited CD38 and the bottom curve shows slow recovery of activity of inhibited enzyme versus time. The absorbance curves with the same equation used for slow-onset: $A_t=v_i t+(v_i-v_f)(1-\exp(-kt))/k+A_0$ where $A_t$ is absorbance, $v_i$ is initial velocity, $v_f$ is final velocity, t is time in s, k is the rate of the recovery rate constant and $A_0$ is the absorbance of the sample at initial time. The rate constant for the recovery phase was obtained from the average value of k determined from the separate fits. The value of $k_{off}$ for 1 was determined to be $1.5\times10^{-5}$ s$^{-1}$ and for 2 was determined to be $2.5\times10^{-5}$ S$^{-1}$.

Calculation of Total Inhibition. Inhibition of CD38 by compounds 1 and 2 could be fully described by the equation $k_{off}/k_{on}*K_i=K_{i(total)}$ for the reactions described by Scheme 5; where $K_{i(total)}$ is the effective dissociation constant between free CD38 and the fully inhibited complex. This equation is valid for slow onset behavior inhibitors and also mechanistic based inactivators of enzymes where a slow recovery of the enzyme from chemical inactivation is present. Using the kinetic parameters in Table 2 the value for $K_{i(total)}$ is 4.5 nM for inhibitor 1. Similarly, a value for $K_{i(total)}$ of 12.5 nM was calculated for inhibitor 2.

TABLE 2

| Linetic and equilibrium parameters for inhibitors 1 and 2. | | |
|---|---|---|
| Parameter | 1 | 2 |
| $K_i$ | 1.2 μM | 4.0 μM |
| $k_{on}$ | $4.2 \times 10^{-3}$ s$^{-1}$ | $8.3 \times 10^{-3}$ s$^{-1}$ |
| $k_{off}$ | $1.5 \times 10^{-5}$ s$^{-1}$ | $2.5 \times 10^{-5}$ s$^{-1}$ |
| $K_{i(total)}$ | 4.5 nM | 12.5 nM |

All values obtained at 19° C. The parameters are defined in accord with Scheme 5. The value for $K_{i(total)}$ was obtained from the relation $K_{i(total)}=(k_{off}/k_{on})*K_i$. The values for each parameter in the calculation is given in the table.

Nature of Inhibition in Slow Phase: Rescue by Base Addition. Our prior investigations of the nature of inhibition of CD38 by ara-F-NMN$^+$ showed it to be governed by both competitive and slow-onset characteristics (Sauve et al., 2000). The slow onset behavior was shown to be a consequence of covalent trapping of the catalytic nucleophile (Glu226) by the ara-F-sugar with nicotinamide leaving group departure. By analogy, the slow-onset inhibition of deoxy-nucleosides 1 and 2 is proposed to proceed via deoxyribose sugar transfer to the catalytic nucleophile. To test this hypothesis, additional chemical methods were used to examine the scheme of inactivation shown in Scheme 6.

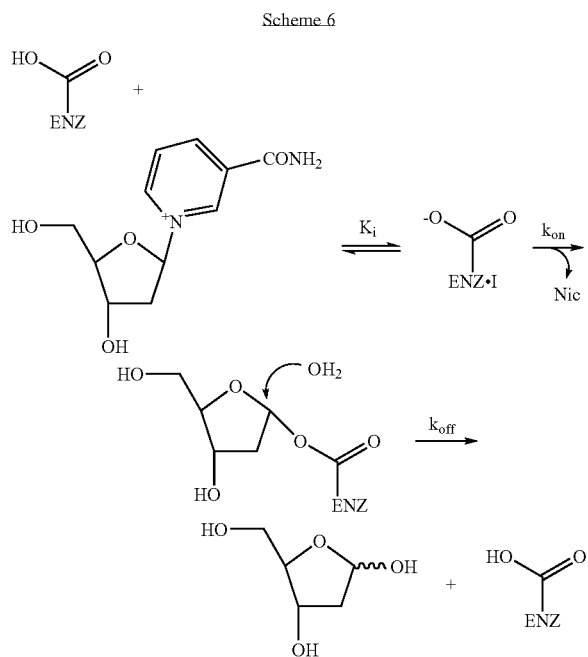

Figure 5:
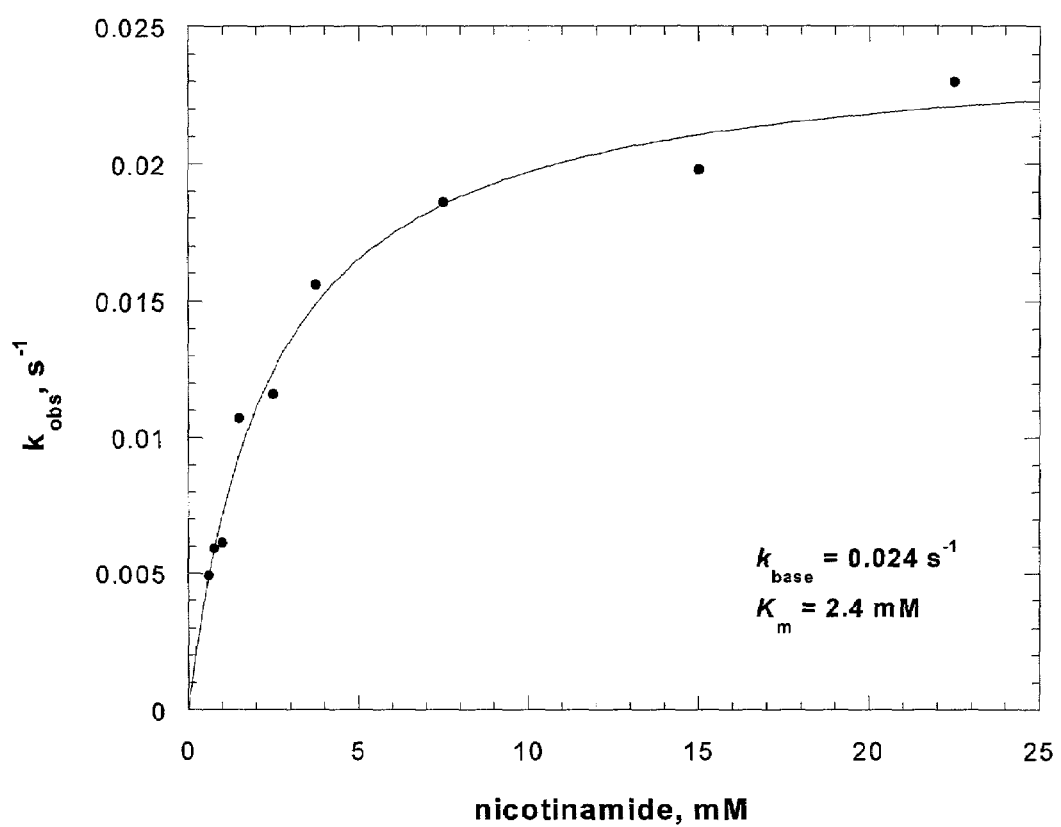
FIG. 5 provides a graph illustrating data measuring rates of CD38 recovery as a function of nicotinamide concentration as determined by stopped flow. The apparent Michaelis parameters were derived from the best fit of the points to the Michaelis-Menten equation. The parameter $k_{base}$ is defined as in Scheme 7.

According to Scheme 6, recovery of enzymatic activity occurs via slow hydrolysis of the covalent intermediate to form deoxyribose and free enzyme. If the covalent intermediate is the normal catalytic reaction path, the enzyme catalytic activity should also be recovered from inhibition by reaction with a substrate nucleophile, such as nicotinamide (Scheme 7). The rate and equilibrium of the reaction will establish the thermodynamic equilibrium of these species. For favorable equilibria, addition of product pyridine bases should permit base-exchange reactions that will rapidly regenerate active enzyme.

covalently inactivated glycosyl transferases (Withers, 2000). Here, the rescue experiment involved preincubation of CD38 with the inhibitor 2 followed by reaction of enzyme with a 300 µM solution of NGD$^+$ containing different concentrations of nicotinamide as a regenerating base. A stopped flow, two syringe fitted spectrophotometer was used to perform the experiments. The fluorescence of cGDPR was measured as a function of time to generate curves that contain an exponential and a linear phase prior to substrate exhaustion. These curves were fit to the equation $F_t=v_f t+ (v_i-v_f)(1-\exp(-kt))/k+F_0$ as previously defined. The rate constant $k_{base}$ was plotted against the nicotinamide concentration to obtain a saturation curve with an apparent $K_m$ value for nicotinamide of 2.4 mM and a maximum rate of 0.023 s$^{-1}$ (FIG. 5). The limiting value of $k_{base}$ as nicotinamide concentration is increased indicates equilibrium binding of nicotinamide at the active site prior to chemical reaction. Therefore, the $K_m$ represents an accurate measurement of $K_d$ for nicotinamide for the covalent form of the enzyme. Similar saturation curves have been reported for the rescue behavior of adenine on 2'-fluoro-adenosine inactivation of adenosine nucleoside transferase (Porter et al., 1995) and for nicotinamide rescue of CD38 from ara-F-NMN$^+$ inactivation (Sauve et al., 2000).

Figure 6:
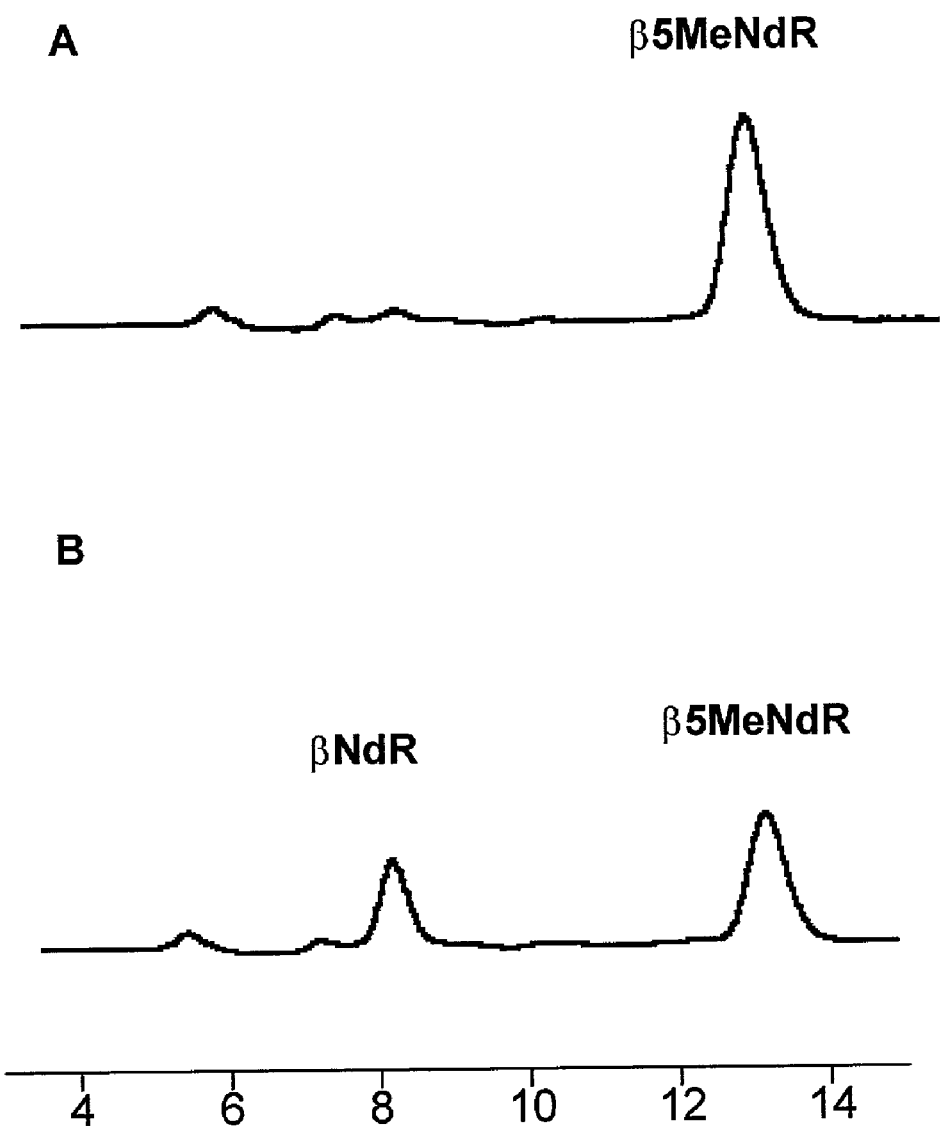
FIG. 6 provides HPLC chromatograms of base exchange reaction solutions. Panel A shows an initial chromatogram at 0 time containing 1 μM CD38, 75 μM 2, and 20 mM nicotinamide. Panel B shows a chromatogram of the same solution after several hours of incubation at 19° C. showing the appearance of the base exchanged product β-nicotinamide-deoxyriboside (Jackson and Bell, 1990). Abbreviations: β5MeNdR; β-5-methylnicotinamide-deoxyriboside, βNdR; β-nicotinamide-deoxyriboside.
Figure 7:
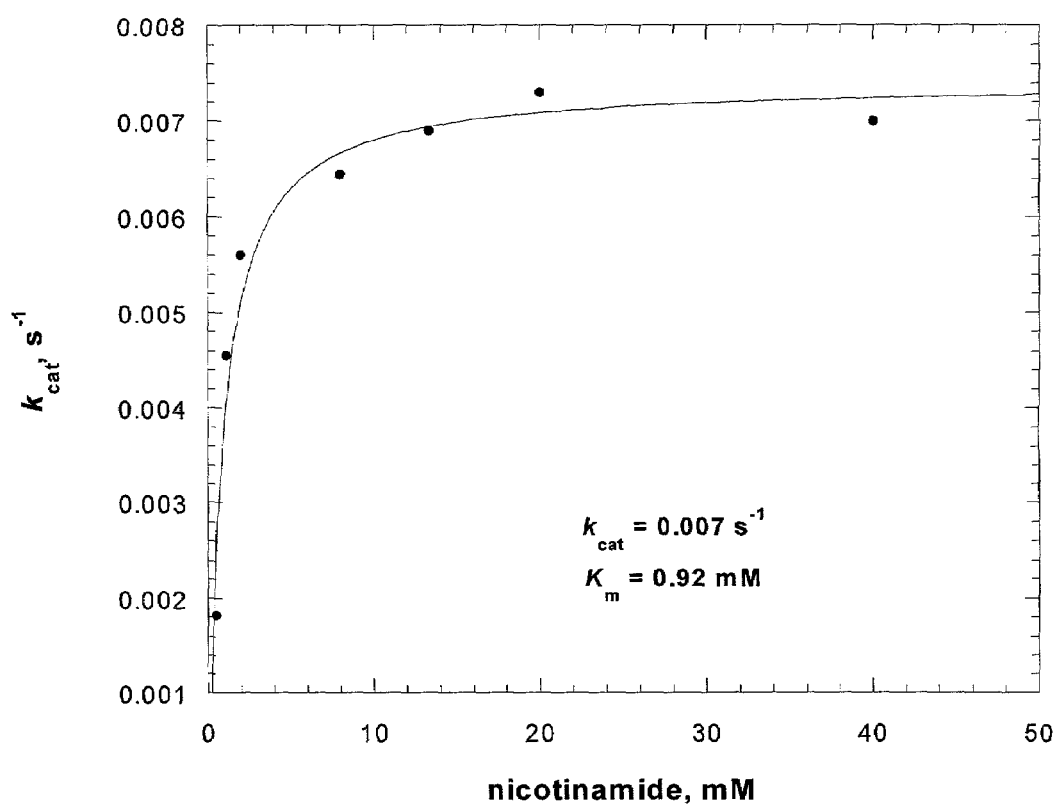
FIG. 7 provides a graph illustrating data showing a steady state rate of base exchange of CD38 in which 2 forms 1 by reaction with nicotinamide. The Michaelis parameters were derived from the best fit of the points to the Michaelis-Menten equation.

Base exchange reaction. The nicotinamide rescue of CD38 enzymatic activity inhibited by 2 completes a catalytic cycle that is proposed to effect base exchange of 2 to form 1. The rescue reaction is the second-half of the normal reaction cycle of the base-exchange reaction catalyzed by CD38, and inactivation of CD38 by 2 is the first half. This hypothesis was tested by incubation of 75 µM 2, with varying concentrations of nicotinamide in the presence of 1 µM CD38 and the reactions monitored by HPLC. FIG. 6 shows that CD38 catalyzes the conversion of 2 to 1 under these conditions. The peak at 8 minutes elutes identically with authentic 1. The rates of these reactions could be monitored by multiple autosampler driven injections and the rates of conversion plotted against nicotinamide concentration. The points were fit using the Michaelis-Menten equation (FIG. 7) to obtain a $K_m$ of 0.92 mM for nicotinamide and a $k_{cat}$ of 0.007 s$^{-1}$. The observed $k_{cat}$ value is within experimental error of the rate of inactivation ($k_{on}$, 0.008 s$^{-1}$, Scheme 5) of CD38 by 2 measured at the same temperature.

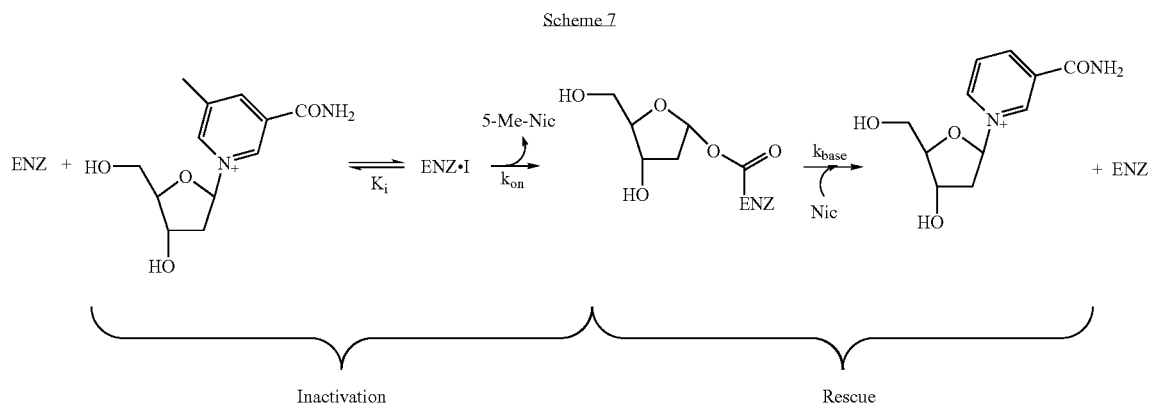

Rescue of activity by substrate nucleophiles has been used as a test of the covalent mechanism in the ara-F-NMN$^+$ inactivation of CD38, with rescue by nicotinamide (Sauve et al., 2000), and has been observed in the covalent inactivation of adenosine nucleoside transferase (36) and other This result establishes that the rate of intermediate formation is rate-limiting in the catalytic cycle of Scheme 7. The greater than two-fold lower $K_m$ for steady state base exchange (0.92 mM) versus the apparent $K_m$ for nicotinamide rescue (2.4 mM) suggests that sub-maximal base binding to the nicotinamide binding pocket during steady state conditions is sufficient to maintain the maximum turnover rate. This notion is supported by the rate constant for formation of the covalent intermediate ($k_{on}$=0.008 s$^{-1}$) and the rate constant for the base reaction step ($k_{base}$=0.023 s$^{-1}$) measured independently.

Figure 8:
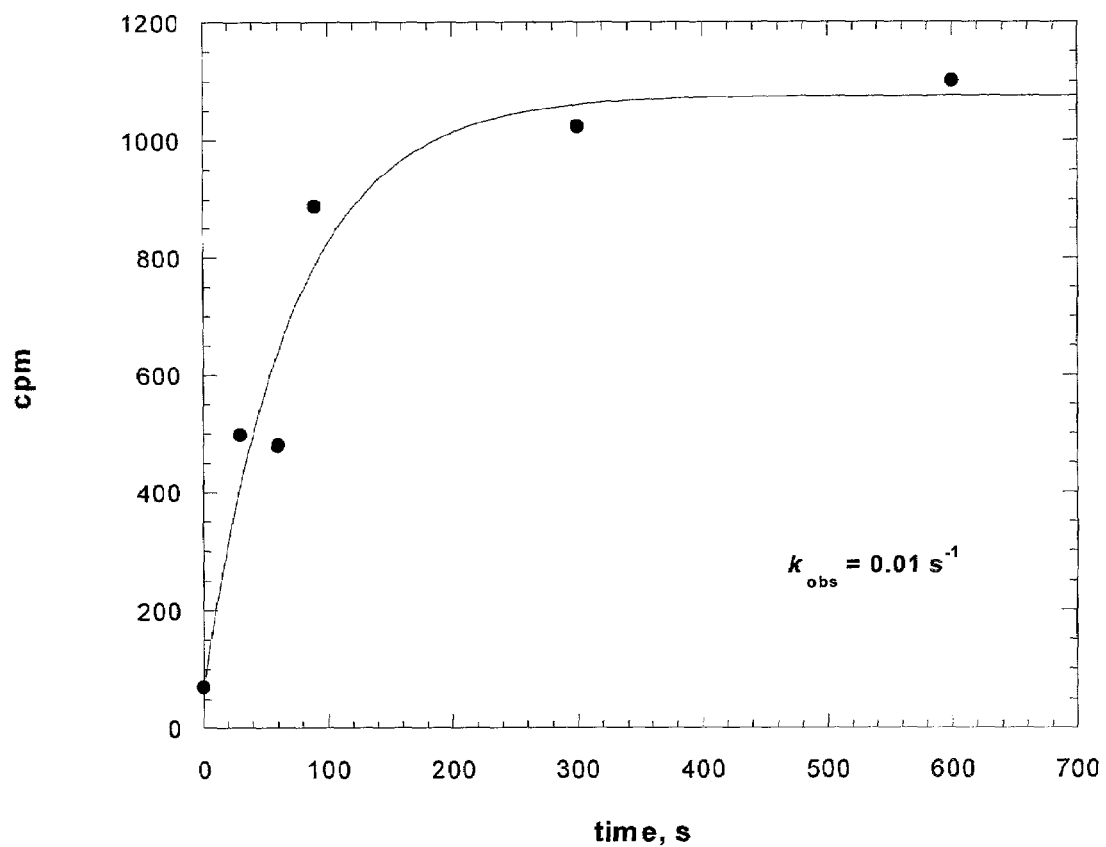
FIG. 8 provides a graph showing radiochemical labeling of one nanomole of CD38 (monomer) by [2-$^3$H]-1 as measured by gel filtration and scintillation counting. The solid curve represents the best fit to the equation P=A+ $A_2\exp(-kt)$. The curve obtains a value of k of 0.01 s$^{-1}$. Specific radioactivity of inhibitor is 866 cpm/nmol.

Titration of Enzyme with [2'-$^3$H]Inhibitor. CD38 inactivation was accomplished using a radiolabeled inhibitor to assess inhibitor interactions with the enzyme independent from inhibition of the catalytic activity. This method allows the determination of the stoichiometry of covalent labeling, and detects cooperativity at multiple sites. The labeling characteristics of CD38 show that it is labeled by 1 in a process governed by a single rate constant with a value of $k_{chem}$0.01 s$^{-1}$ at 25° C. (FIG. 8) within reasonable agreement with the rate constant for inactivation in kinetic assays of inhibition ($k_{on}$=0.0042 s$^{-1}$ at 19° C.). The extent of labeling does not change after the first 20 minutes of incubation time, which indicates that there is no non-specific labeling of the enzyme by the inhibitor. According to specific activity measurements and protein concentration, the labeling is 1:1 versus CD38 monomer concentration. This result is similar to what was observed with CD38 inhibition by ara-F-NMN$^+$ (Sauve et al., 2000).

Discussion

Deoxyriboside nicotinamide derivatives bind to the catalytic sites of CD38 with higher binding affinity than the natural substrate, NAD$^+$. 1 has a binding constant of 1.2 μM and 2 has a binding constant of 4 μM. In comparison the $K_m$ for dinucleotide and mononucleotide substrates is 150 μM for NMN$^+$ (Sauve et al., 1998) 15 μM for NAD$^+$ and 2.5 μM for NGD$^+$. Based on these comparisons, it is apparent that truncation of structure does not necessarily weaken binding. Inhibition of CD38 by the deoxynucleoside compounds 1 and 2 is not only competitive, but is characterized by a second kinetic phase of inhibition marked by enhanced affinity of the inhibitor for the enzyme with rates of onset of 0.004 s$^{-1}$ for 1 and 0.008 s$^{-1}$ for 2. Recovery of the enzyme from the second phase of binding is quite slow, on the order of 2×10$^{-5}$ s$^{-1}$ at 19°C., and was similar within experimental error for both 1 and 2. By use of the equation for slow onset inhibitors, $K_i k_{off}/k_{on}=K_{i(total)}$, the enhanced binding leads to inhibition values of 4.5 nM for inhibition of CD38 by 1 and 12.5 nM by 2. These inhibition constants are lower than any known CD38 inhibitors and confirm that highly abbreviated structures can rapidly and potently inhibit ADP-ribosyl cyclase enzymes. The magnitude of the rate constants for inactivation ($k_{on}$) show that tight inhibition can be achieved within minutes at physiological temperatures.

The nature of the slow-phase process leading to formation of the tight complex in Scheme 5 is proposed to be the covalent modification of the enzyme by inhibitor via attachment of the deoxyribose sugar to the enzyme catalytic nucleophile as shown in Scheme 6. A previous example of covalent modification of CD38 revealed that the inhibitor ara-F-NMN$^+$ forms a stable ara-F-ribose-5-phosphate ester with Glu226 (Sauve et al., 2000). MS studies confirmed the identity of this acid as the catalytic nucleophile. This residue is universally conserved across all ADP-ribosyl cyclase sequences, and has been mutagenized with ablation of catalytic activity for CD38 (Munshi et al., 1999). The covalent modification was shown to be reversible, and nicotinamide additions to the trapped enzyme recover catalytic activity and reform ara-F-NMN$^+$. Moreover, CD38 catalyzes base exchange using ara-F-NMN$^+$ as a substrate.

Similar behaviors were observed for inhibited CD38 treated with the deoxy-inhibitors 1 and 2. For instance, when fully inhibited CD38 enzyme (by either 1 or 2) was treated with millimolar concentrations of nicotinamide, recovery of catalytic activity was observed, with a rate of recovery dependent on nicotinamide concentration. The recovery rate reached a saturable maximum versus nicotinamide concentration. Rate saturation for recovery has also been observed in previous studies of covalent intermediates and the apparent $K_m$ appears to reflect the binding affinity of the rescue nucleophile within the active site. This value was found to be 17 mM for ara-F-NMN$^+$ rescue by nicotinamide (Sauve et al., 2000), and the 2.4 mM value for rescue from the deoxyribose intermediate indicates that nicotinamide binding is tighter in the covalent complex formed by deoxyribose modification of CD38.

Scheme 7 shows inactivation and recovery as two mechanistic steps in a catalytic cycle that leads to inhibitor base exchange. Incubations of 2 with nicotinamide confirmed that CD38 catalyzes base exchange to form 1 and 5-methylnicotinamide. HPLC analysis was used to monitor the kinetics of base exchange because 1 is readily separated from 2 and base exchange is fairly slow. The $K_m$ of nicotinamide for base exchange is 0.92 mM and the $k_{cat}$ is 0.007 s$^{-1}$ at 19° C. The value of $K_m$ for base exchange (0.92 mM) is significantly lower than the value for the apparent $K_m$ for base rescue (2.4 mM) of CD38 activity from inhibition by 2. However, the rate of rescue saturates at 0.024 s$^{-1}$, suggesting the lower $K_m$ for exchange takes its origin from chemistry of covalent modification of the enzyme being rate limiting in the catalytic cycle, and because full site binding by base is unnecessary to maintain the steady state rate in the second reaction of base exchange. Thus, the rate of turnover of base exchange matches the rate of slow-phase inhibitor inactivation by 2, which has the value 0.008 s$^{-1}$.

Radiochemical titrations of enzyme with [2'-$^3$H]-1 confirm that labeling reaches maximum with a rate constant of 0.01 s$^{-1}$ and extended incubations do not increase radiochemical labeling. The extent of labeling is consistent with a ratio of inhibitor to subunit of 1:1. These measurements confirm that covalent modification is a specific process and is due to the covalent modification of the catalytic nucleophile responsible for catalysis with faster substrates.

The effectiveness of deoxy-nucleosides as trapping agents for CD38 is in contrast to chemical stability profiles. 2'-Deoxy derivatives are intrinsically more labile to uncatalyzed solvolysis reactions than the corresponding ribose derivatives, and even more unstable than 2'-fluorine substituted derivatives (Oppenhemer and Handlon, 1992). Trapping of covalent intermediates on nucleoside and glycosyl transferase enzymes has been successful in a number of cases by the introduction of 2'-fluorine (Sauve et al., 2000; Porter et al., 1995; Withers, 2000), because of the electronic destabilization of the cationic charge that builds up at the anomeric carbon in transition states common to nucleoside and glycosyl transfer reactions. The increase in energy of these transition states retards breakdown of trapped intermediates (Withers, 2000). In examination of the rate of turnover of NMN$^+$ versus ara-F-NMN$^+$ on CD38 it was intriguing to note the ratio of the rates of turnover of CD38 covalent intermediates was on the order of 10$^7$ at 37° C. (Sauve et al., 2000; Withers, 2000) which did not match the ratio of their uncatalyzed solvolysis rates, which was measured to be 30:1 at the same temperature (Oppenhemer and Handlon, 1992). This suggested that slow turnover of fluorine substituted intermediates by CD38 took most of its origin from removal of the 2'-OH group and not from an electronic effect contributed by fluorine.

The results of this study strongly corroborate this viewpoint. In this case removal of the 2'-OH and replacement with a hydrogen atom in conjunction with removal of the 5'-phosphate group leads to efficient formation of the covalent intermediate but inefficient hydrolytic turnover of this species, leading to effective trapping and inhibition of the enzyme. The role of the 2'-OH in catalysis is suggested by the proximity it normally has to the Glu226 leaving group which departs the sugar in intermediate breakdown. Both share the alpha face of the sugar and proton transfer to the Glu residue during catalytic turnover may be mediated in part by the 2'-OH. The proposed protonation state of the catalytic Glu during catalysis is indicated in Scheme 6. Although this rationale deserves additional investigation a strong Glu -2'OH interaction has been proposed as a part of NAD$^+$ glycohydrolase function (Oppenhemer and Handlon, 1992) and has recently been revealed crystallographically in the enzyme BST-1 (Yamamoto-Katayama et al., 2002).

Trapping efficiency can also improve from the lack of the ADP group in inhibitors 1 and 2. The nucleoside structure lacks the adenylate of the normal NAD$^+$ substrate thus precluding the normal cyclization pathway inherent to dinucleotide substrates. The absence of a reasonable nucleophile for an escape from the intermediate complex via the intramolecular route leaves hydrolysis as the only remaining escape pathway.

In conclusion, deoxynucleosides are effective mechanism based inhibitors of CD38 through formation of a covalent intermediate that has been identified as part of the normal reaction coordinate of CD38 catalysis. A variety of techniques establish that this inactivation is specific to a single reactive moiety on the enzyme, which is catalytically competent to support the base exchange mechanism inherent to CD38 catalysis with faster substrates. These compounds lack phosphate groups, have nanomolar binding affinity for CD38 enzymes, inactivate within minutes at room temperature and have slow recovery rates, suggesting that these derivatives may be effective probes of CD38 biochemical action in cells and tissues.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound represented by the formula:

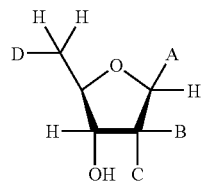

wherein A is selected from the group consisting of i, ii, iii, iv, v, vi, vii and viii, wherein i, ii, iii, iv, v, vi, vii and viii are the following:

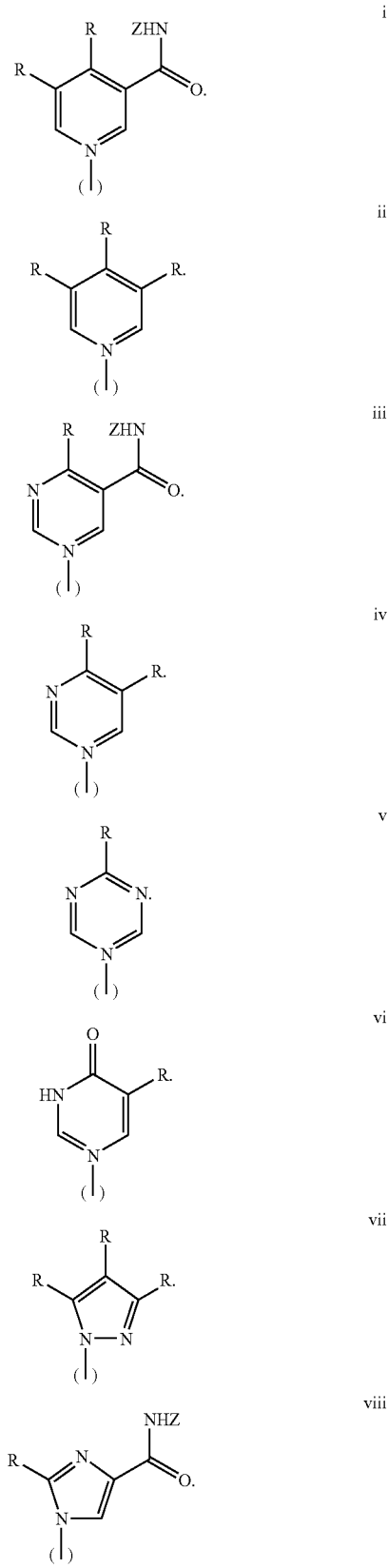

wherein each R is independently H or an electron-contributing moiety selected from methyl, ethyl, O-methyl, amino, NMe$_2$, hydroxyl, CMe$_3$, aryl or C3–C10 alkyl, provided at least one R is an electron contributing moiety, Z is a hydrogen, alkyl, aryl, hydroxyl, amino, OZ' where Z' is an alkyl or aryl, NHZ' where Z' is an alkyl or aryl, or NHZ'Z" where Z' and Z" are independently an alkyl or aryl;

B is hydrogen, or a halogen, amino, or thiol group;

C is hydrogen, or a halogen, amino, or thiol group; and

D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge.

2. The compound of claim 1, wherein the electron contributing moiety is NMe$_2$, hydroxyl, CMe$_3$, aryl or C3–C10 alkyl.

3. The compound of claim 1, wherein the electron contributing moiety is methyl, ethyl, O-methyl or amino.

4. The compound of claim 1, wherein the electron contributing moiety is a methyl.

5. The compound of claim 1, wherein A further comprises a second electron contributing moiety selected from methyl, ethyl, O-methyl, amino, NMe$_2$, hydroxyl, CMe$_3$, aryl or C3–C10 alkyl.

6. The compound of claim 1, wherein A is i, ii, vii or viii.

7. The compound of claim 1, which is a methyl-nicotinamide-2'-deoxyriboside.

8. The compound of claim 1, which is a 5-methyl-nicotinamide-2'-deoxyriboside.

9. The compound of claim 1, which is β-1'-5-methyl-nicotinamide-2'-deoxyribose, β-D-1'-5-methyl-nicotinamide-2'-deoxyribofuranoside, β-1'-4,5-dimethyl-nicotinamide-2'-deoxyribose or β-D-1'-4,5-dimethyl-nicotinamide-2'-deoxyribofuranoside.

10. The compound of claim 1, which is β-1'-5-methyl-nicotinamide-2'-deoxyribose.

11. The compound of claim 1, wherein both B and C are hydrogen, or either B or C is a halogen, amino, or thiol group and the other of B or C is hydrogen.

12. The compound of claim 1, wherein D is a primary alcohol or hydrogen.

13. The compound of claim 1 represented by the formula:

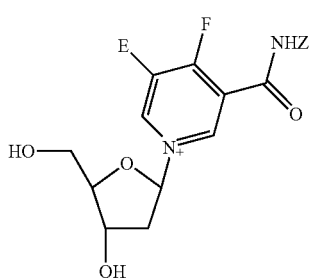

I wherein Z is a hydrogen, alkyl, aryl, hydroxyl, amino, OZ' where Z' is an alkyl or aryl, NHZ' where Z' is an alkyl or aryl, or NHZ'Z" where Z' and Z" are independently an alkyl or aryl; E and F are independently H, CH$_3$, OCH$_3$, CH$_2$CH$_3$, NH$_2$, OH, NHCOH, NHCOCH$_3$, N(CH$_3$)$_2$, C(CH$_3$)$_2$, an aryl or a C3–C10 alkyl, provided that, when either of E or F is H, the other of E or F is not H.

14. The compound of claim 13, wherein E and F are independently H, CH$_3$, OCH$_3$, or OH, provided that, when either of E or F is H, the other of E or F is not H.

15. A pharmaceutical composition comprising the compound of claim 1 and a pharmaceutically-acceptable carrier.

16. A compound represented by the formula:

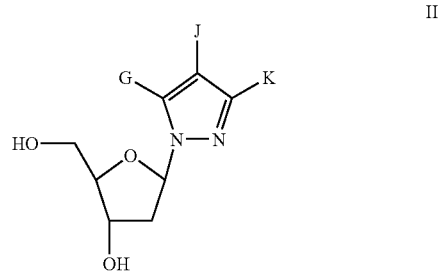

II wherein either G, J or K is CONHZ, wherein Z is a hydrogen, an alkyl, an aryl, a hydroxyl, an amino, OZ' where Z' is an alkyl or aryl, NHZ' where Z' is an alkyl or aryl, or NHZ'Z" where Z' and Z" are independently an alkyl or an aryl; and the other two of G, J and K is independently CH$_3$, OCH$_3$, CH$_2$CH$_3$, NH$_2$, OH, NHCOH, or NHCOCH$_3$.

17. A compound represented by the formula:

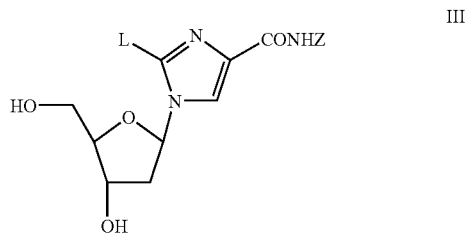

III wherein Z is a hydrogen, an alkyl, an aryl, a hydroxyl, an amino, OZ' where Z' is an alkyl or aryl, NHZ' where Z' is an alkyl or aryl, or NHZ'Z" where Z' and Z" are independently an alkyl or an aryl; and L is CH$_3$, OCH$_3$, CH$_2$CH$_3$, NH$_2$, OH, NHCOH, or NHCOCH$_3$.

18. The compound of claim 1, which is β-D-1'-5-methyl-nicotinamide-2'-deoxyribofuranoside.

19. The compound of claim 1, which is β-1'-4,5-dimethyl-nicotinamide-2'-deoxyribose.

20. The compound of claim 1, which is β-D-1'-4,5-dimethyl-nicotinamide-2'-deoxyribofuranoside.

21. A pharmaceutical composition comprising the compound of claim 16 and a pharmaceutically-acceptable carrier.

22. A pharmaceutical composition comprising the compound of claim 17 and a pharmaceutically-acceptable carrier.

23. The compound of claim 13, wherein Z is hydrogen.

24. The compound of claim 13, wherein E and F are independently H, CH$_2$CH$_3$ or a C3–C10 alkyl, provided that, when either of E or F is H, the other of E or F is not H.

25. The compound of claim 16, wherein J or K is CONHZ.

26. The compound of claim 25, wherein Z is hydrogen.

27. The compound of claim 16, wherein the other two of G, J and K is independently CH$_3$, OCH$_3$, CH$_2$CH$_3$ or OH.

28. The compound of claim 17, wherein Z is hydrogen.

29. The compound of claim 17, wherein L is CH$_3$, OCH$_3$, CH$_2$CH$_3$ or OH.

* * * * *